(12) United States Patent
Isaacson et al.

(10) Patent No.: US 10,926,028 B2
(45) Date of Patent: Feb. 23, 2021

(54) FLUID TRANSFER DEVICE OR SET WITH RETRACTABLE NEEDLE AND SEPTUM

(71) Applicant: Becton, Dickinson and Company, Franklin Lakes, NJ (US)

(72) Inventors: S. Ray Isaacson, Layton, UT (US); Ralph L. Sonderegger, Sr., Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 95 days.

(21) Appl. No.: 16/269,323

(22) Filed: Feb. 6, 2019

(65) Prior Publication Data

US 2019/0167896 A1 Jun. 6, 2019

Related U.S. Application Data

(62) Division of application No. 14/326,032, filed on Jul. 8, 2014, now Pat. No. 10,232,110.

(51) Int. Cl.
*A61M 5/162* (2006.01)
*A61M 25/06* (2006.01)
(Continued)

(52) U.S. Cl.
CPC .......... *A61M 5/1626* (2013.01); *A61M 5/158* (2013.01); *A61M 25/0631* (2013.01);
(Continued)

(58) Field of Classification Search
CPC .... A61M 5/158; A61M 5/162; A61M 5/1626; A61M 25/0637; A61M 25/0631; A61M 2005/1586; A61M 2039/042; A61M 39/04
See application file for complete search history.

(56) References Cited

U.S. PATENT DOCUMENTS

| 5,613,500 A | 3/1997 | Bishop |
| 6,641,555 B1 | 11/2003 | Botich et al. |

(Continued)

FOREIGN PATENT DOCUMENTS

| CN | 201364409 | 12/2009 |
| CN | 101678192 | 3/2010 |

(Continued)

*Primary Examiner* — Tiffany Legette
(74) *Attorney, Agent, or Firm* — Kirton & McConkie; Craig Metcalf; Kevin Stinger

(57) ABSTRACT

A sealed fluid transfer device comprised of tubing, a proximal fitting, and a distal needle assembly is provided. The needle assembly includes a needle hub secured to a needle cannula. A cantilevered actuator arm extends outwardly from the needle hub having an actuator button at its free end. The needle assembly is disposed in a barrel and can move from a distal position, where the needle is exposed, to a proximal position, where the needle is shielded. The barrel includes a septum which seals the barrel. A spring is disposed in the barrel for propelling the needle assembly to the proximal position. The barrel includes an aperture that receives the actuator button for locking the spring in a compressed condition. Depression of the actuator button enables the spring to propel the needle assembly into its proximal position. A safety mechanism prevents inadvertent depression of the actuator button.

15 Claims, 22 Drawing Sheets

(51) Int. Cl.
*A61M 5/158* (2006.01)
*A61M 39/04* (2006.01)

(52) U.S. Cl.
CPC ......... *A61M 39/04* (2013.01); *A61M 25/0637* (2013.01); *A61M 2005/1585* (2013.01); *A61M 2039/042* (2013.01)

(56) References Cited

U.S. PATENT DOCUMENTS

| | | |
|---|---|---|
| 7,294,118 B2 | 11/2007 | Saulenas et al. |
| 7,691,083 B2 | 4/2010 | Botich et al. |
| 8,109,905 B2 | 2/2012 | Saulenas et al. |
| 8,308,685 B2 | 11/2012 | Botich et al. |
| 2003/0078540 A1* | 4/2003 | Saulenas ........... A61M 25/0631 604/110 |
| 2003/0181862 A1 | 9/2003 | Lin |
| 2004/0186426 A1* | 9/2004 | Allard .............. A61B 5/150732 604/110 |
| 2007/0112333 A1 | 5/2007 | Hoang et al. |
| 2013/0218093 A1* | 8/2013 | Markussen ......... A61M 5/2033 604/198 |

FOREIGN PATENT DOCUMENTS

| | | |
|---|---|---|
| CN | 202459844 | 10/2012 |
| CN | 103124578 | 5/2013 |
| EP | 599564 | 6/1994 |
| JP | 2002210018 | 7/2002 |
| JP | 2003180829 | 7/2003 |
| JP | 2003339857 | 12/2003 |
| JP | 2008531237 | 8/2008 |
| JP | 2010522629 | 7/2010 |
| WO | 2013/027355 | 2/2013 |

\* cited by examiner

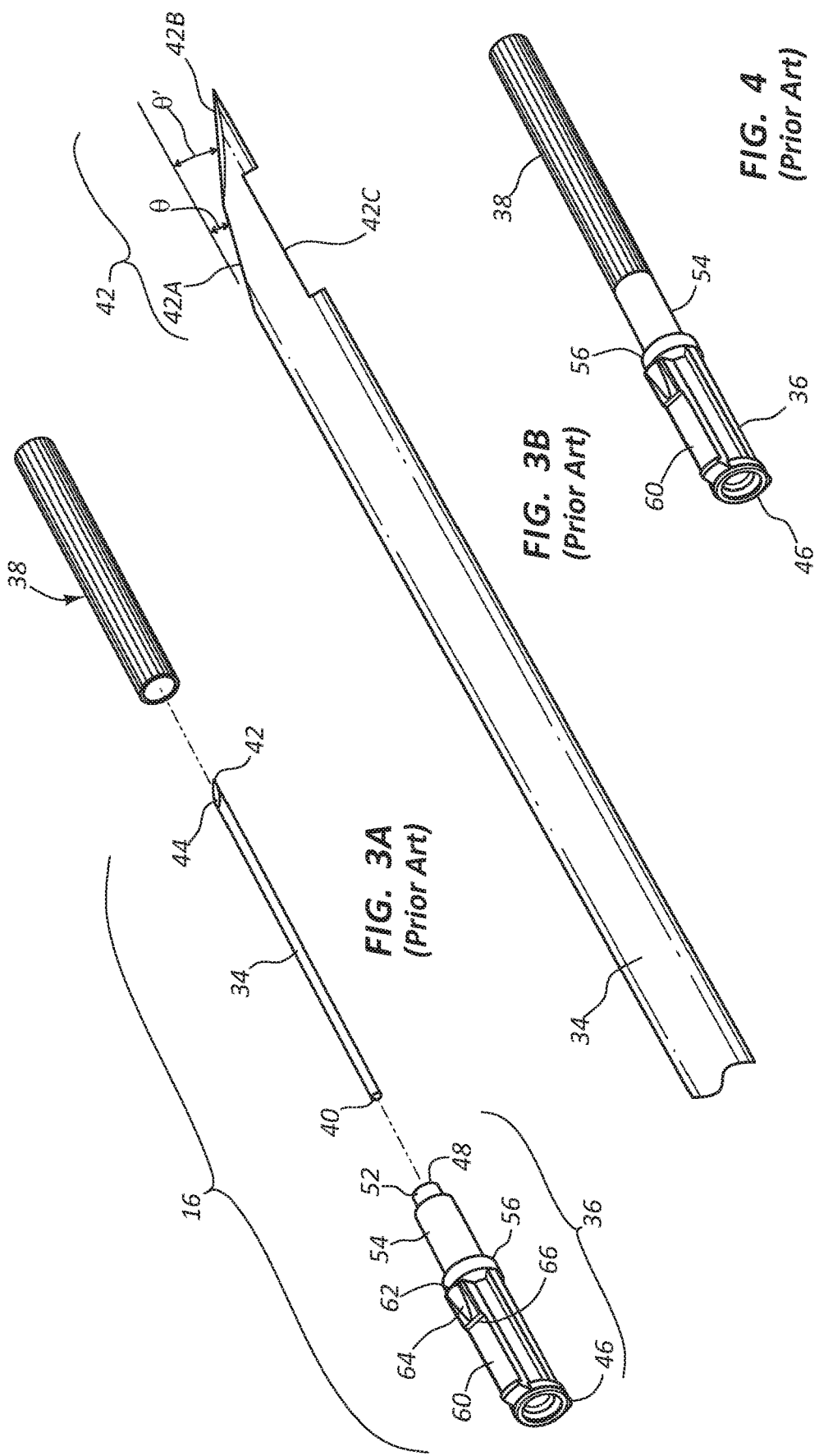

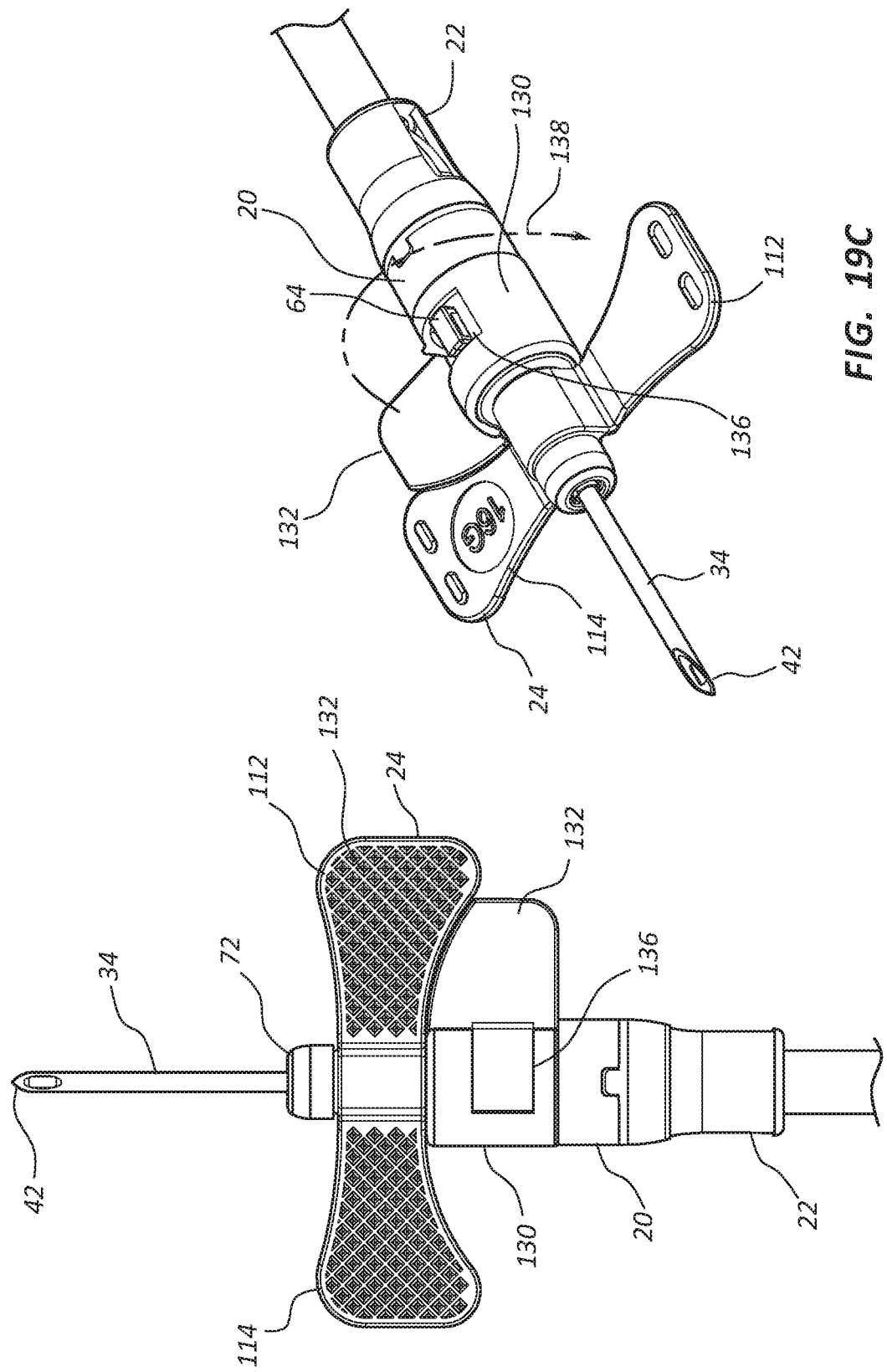

FLUID TRANSFER DEVICE OR SET WITH RETRACTABLE NEEDLE AND SEPTUM

RELATED APPLICATIONS

This application is a divisional of U.S. application Ser. No. 14/326,032, filed Jul. 8, 2014, entitled FLUID TRANSFER DEVICE OR SET WITH RETRACTABLE NEEDLE AND SEPTUM, which is incorporated herein in its entirety.

FIELD OF THE INVENTION

The present invention relates to a fluid transfer device for transferring fluid to or from a patient, and more particularly to a fluid transfer device having a retractable needle and a sealing septum.

BACKGROUND OF THE INVENTION

Various types of medical devices employ a needle for piercing the skin of a patient for diagnostic or therapeutic purposes. One such fluid transfer device is a fluid collection device which includes a needle for piercing a blood vessel or other part of the patient to allow a fluid, for example, blood, to be sampled from a patient. When the needle is inserted into the patient, blood or other fluid is withdrawn through the needle, for example, into a vacuum collection tube. Handling of such needle-bearing medical devices after the needle is withdrawn from the patient can result in the unwanted transmission of various pathogens thereby exposing medical personnel and possibly others to serious or fatal illness due to an inadvertent needle stick injuries as well as other blood borne pathogens exposed through fluid or blood which leaks out of the device following use and removal from the patient.

BRIEF SUMMARY OF THE INVENTION

In light of the foregoing, the present invention provides a medical device having a hollow housing and a needle with a sharpened tip. The needle is operable between an extended, or active position, and a retracted, or inactive position. The sharpened tip projects forwardly from the housing in the extended position, with the sharpened tip being sealably enclosed within the housing in the retracted position. Initially, a needle retainer selectively retains the needle in the extended position. A biasing element biases the needle toward the retracted position. An actuator actuates the needle retainer to release the needle so that the biasing element propels the needle rearwardly toward the retracted position. A rearward stop connected with the needle is operable to retain the needle against continued rearward displacement after the needle is retracted. In some embodiments, a forward stop connected with the needle is operable to retain the needle against forward displacement after the needle is retracted.

According to some embodiments, a sealed fluid transfer device comprised of tubing, a proximal fitting, and a sealed retractable distal needle assembly is provided. In some embodiments, the needle assembly includes a needle hub and a needle cannula securely coupled to the needle hub. The needle assembly also includes a resiliently deflectable actuator arm extending from the needle hub and having an actuator button formed at the free end thereof. According to some embodiments, the needle assembly is slidably disposed in a barrel assembly or housing having proximal and distal ends and a passage extending therebetween. In such embodiments, the needle assembly and the actuator arm are axially movable relative to the barrel. In a distal position, the needle cannula projects distally beyond the distal end of the barrel. In a proximal position, the needle cannula is entirely contained within the barrel.

The barrel further defines an actuating aperture extending through a side of the barrel. According to various embodiments, the barrel aperture engages the actuator button when the needle assembly is in the distal position. However, the actuator button disengages the aperture when the actuator arm is resiliently deflected.

The device further includes a spring that is disposed in the barrel assembly. The spring provides a biasing force for retracting the needle assembly to the proximal position when the actuator arm is deflected and the actuator button disengages the barrel aperture.

In various embodiments, the device also includes a septum fitted within the distal end of the barrel. When the needle assembly occupies the distal position, the needle cannula extends through the septum via a slit preformed therein. When the needle assembly is retracted to the proximal position, the needle cannula is withdrawn from the septum slit, whereby the septum seals the barrel assembly to prevent blood or other fluid from exiting therefrom.

According to some embodiments, the device also includes an absorbent sponge. The sponge is fitted in proximity to the septum within the distal end of the barrel. When the needle assembly is in the distal position, the needle cannula extends through the sponge. However, as the needle assembly is retracted, the sponge absorbs and retains any fluid that is squeegeed or removed from the outer surface of the needle as it is withdrawn through the septum.

In some embodiments, a two-step process is required to disengage the needle assembly such that it can be retracted under spring force into the proximal position. For example, in some embodiments the device includes an annular sleeve rotatably disposed about a circumference of the proximal end of the barrel. In such embodiments, the sleeve is selectively rotatable between a first position and a second position. The safety cover obscures the barrel aperture and the actuator button when the sleeve is in the first position. However, when the sleeve is rotated into the second position, the barrel aperture and the actuator button are exposed and accessible through an access slot of the sleeve. Thus, the first position of the sleeve prevents the needle assembly from being inadvertently retracted into the proximal position. Rather, the sleeve must be rotated to the second position to expose the actuator arm. Once exposed, the actuator arm may be deflected by the user in order to disengage the actuator button from the barrel aperture. The actuator arm is then deflected and the needle assembly is retracted under spring force into the proximal position.

In other embodiments, the actuator button includes a first interlocking edge for interacting with a second interlocking edge of the barrel aperture. In such embodiments, the first and second interlocking edges interlock when the needle hub is in the distal position, whereby the actuator button engages the barrel aperture. In such embodiments, the spring biases the first and second interlocking edges into an interlocked engagement when the needle assembly is in the distal position. The interlocked engagement of the first and second interlocking edges prevents the needle assembly from being inadvertently retracted into the proximal position. Accordingly, the needle assembly must be advanced distally by the user until the interlocking edges disengage. Once disengaged, the actuator arm can be deflected, thereby disengaging the actuator button from the barrel aperture and causing the needles assembly to retract under spring force into the proximal position.

BRIEF DESCRIPTION OF THE SEVERAL VIEWS OF THE DRAWINGS

In order that the manner in which the above-recited and other features of the invention are obtained will be readily understood, a more particular description of the invention briefly described above will be rendered by reference to specific embodiments thereof which are illustrated in the appended drawings. These drawings depict typical embodiments of the invention and are not, therefore, to be considered to limit the scope of the invention.

FIG. 3A is an exploded perspective view of a needle assembly.

FIG. 3B is a side elevation view of a needle.

FIG. 4 is a perspective view of the needle assembly in its assembled condition.

FIG. 19B is a bottom view of the distal end of the device illustrated in FIG. 19A.

FIG. 19C is another perspective view of the distal end of the device illustrated in FIG. 19A having the safety sleeve rotated into a second position.

DETAILED DESCRIPTION OF THE INVENTION

Figure 1:
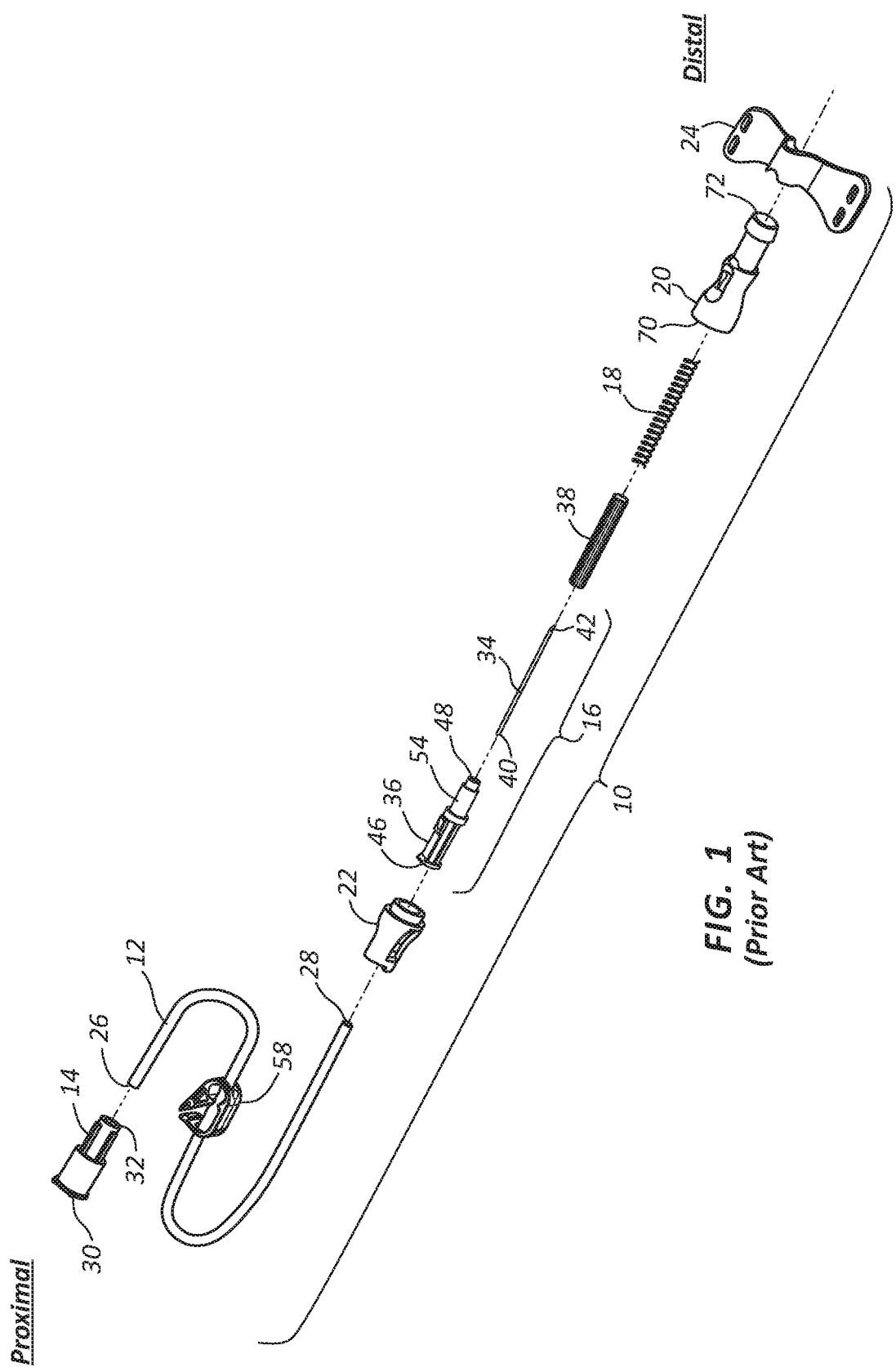
FIG. 1 is an exploded perspective view of a prior art fluid collection or infusion device or set in accordance with some embodiments of the invention.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Moreover, in the drawings, the dimensions of particular components or elements are for illustrative purposes only and may be exaggerated for clarity. Thus, the following more detailed description, as represented in the figures, is not intended to limit the scope of the invention as claimed, but is merely representative of presently preferred embodiments of the invention.

As used herein, the term "proximal" refers to a location with respect to the device during normal use that is closest to the clinician and farthest from the patient. Conversely, the term "distal" refers to a location with respect to the device during normal use that is farthest from the clinician and closest to the patient. As used herein, the term "top", "up" or "upwardly" refers to a location with respect to the device during normal use that is radially away from the longitudinal axis of the device and away from the patient's skin. Conversely, as used herein, the term "bottom", "down" or "downwardly" refers to a location with respect to the device during normal use that is radially away from the longitudinal axis of the device and toward the patient's skin. As used herein, the term "in" or "inwardly" refers to a location with respect to the device during normal use that is toward the inside of the device. Conversely, as used herein, the term "out" or "outwardly" refers to a location with respect to the device during normal use that is toward the outside of the device.

Figure 2:
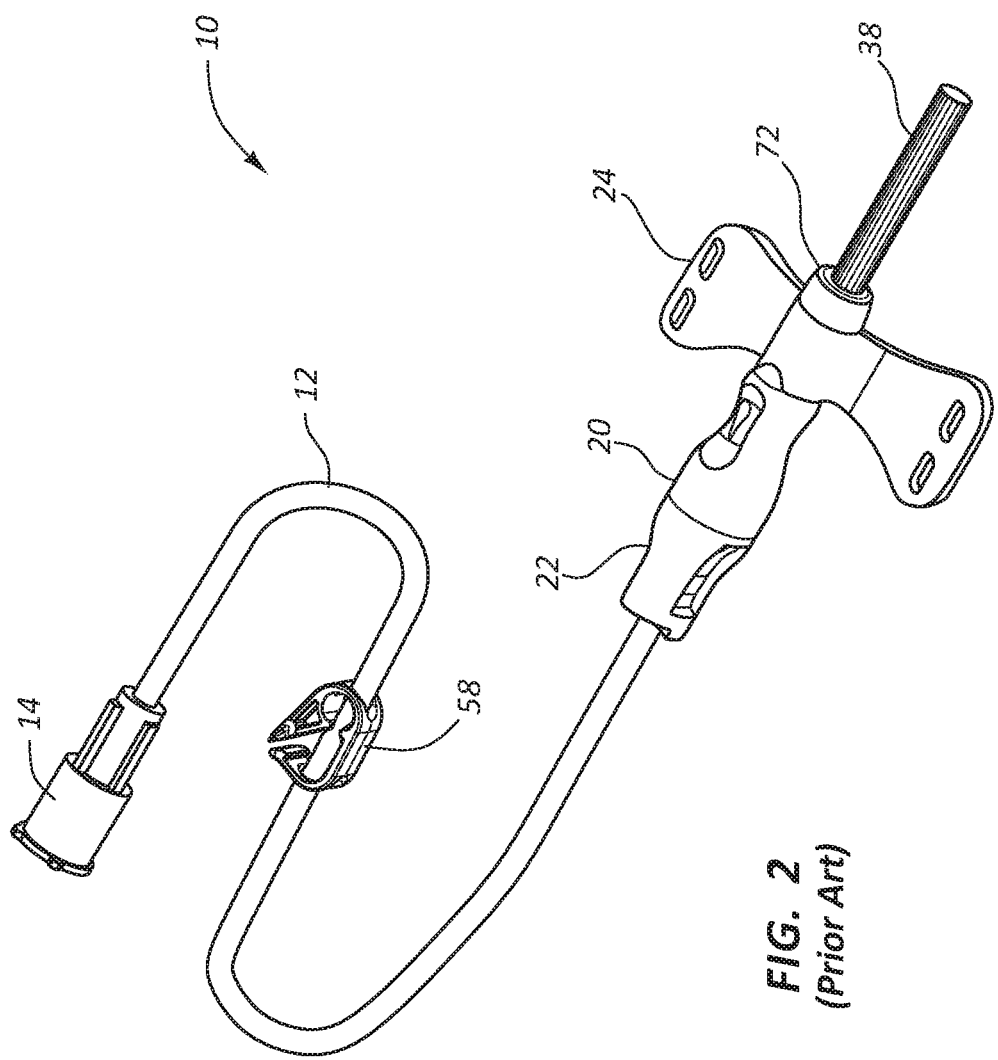
FIG. 2 is a perspective view of the fluid collection or infusion device or set in its assembled condition.
Figure 5:
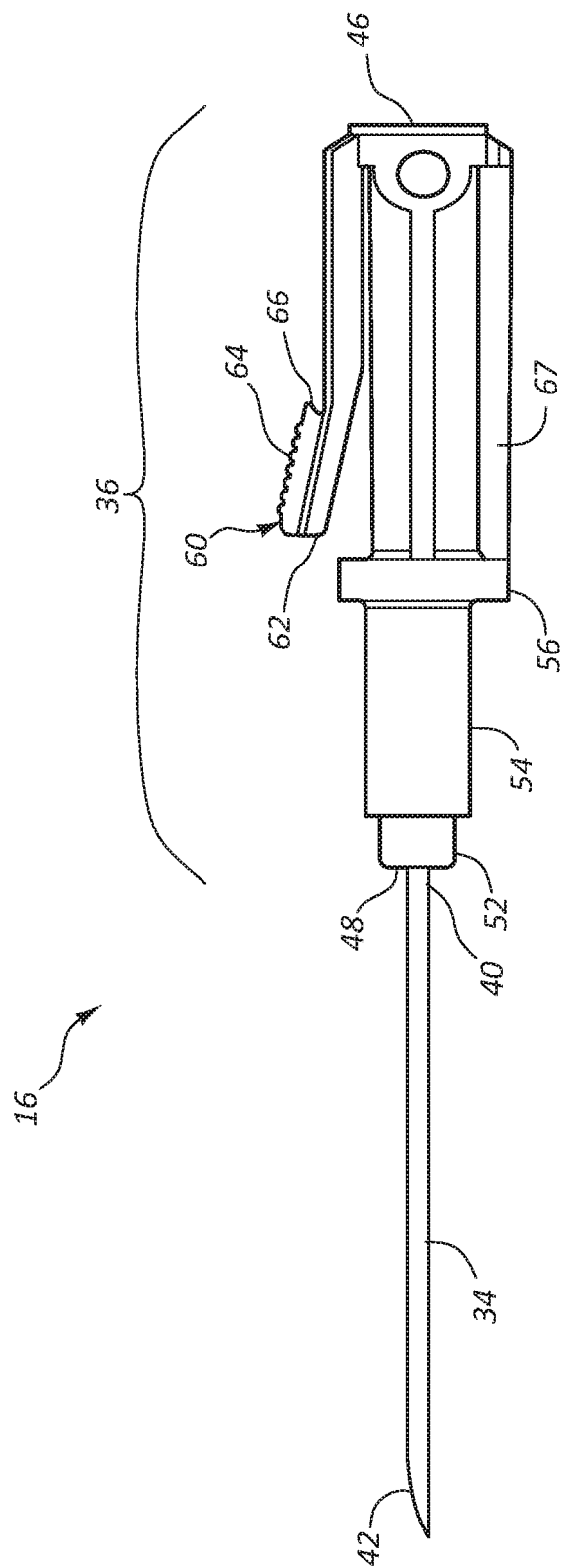
FIG. 5 is a side elevation view of a prior art needle assembly.
Figure 6:
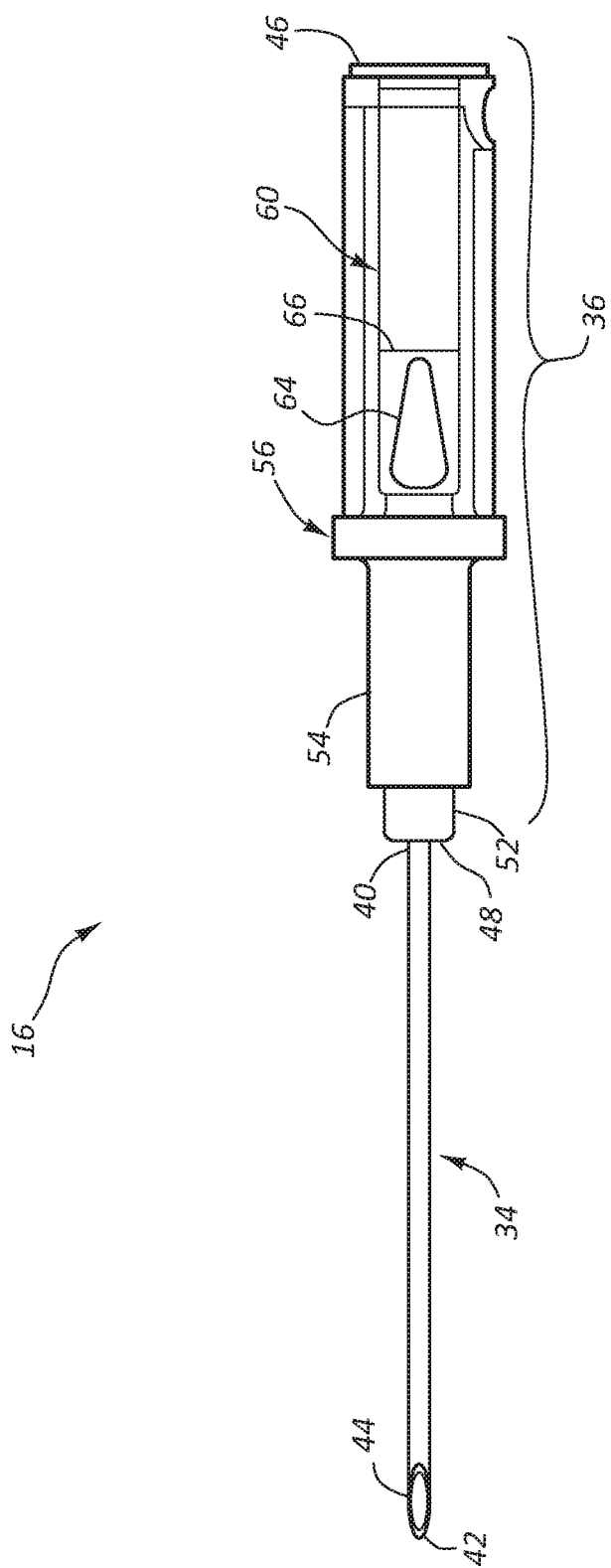
FIG. 6 is a top plan view of the needle assembly.

Referring now to FIGS. 1 and 2, and particularly to FIG. 1, an implementation of a fluid collection or infusion device or set 10, also referred to herein as a fluid transfer device, set, or assembly, is shown. According to various embodiments, device 10 generally includes a length of flexible plastic or rubber tubing 12, a proximal fitting or connector 14, a needle assembly 16, a needle protector 38, a spring 18, a barrel or housing assembly that comprises a distal barrel 20, a proximal barrel 22, and a wing attachment 24, and a clamp or fluid control or flow restricting device 58.

Tubing 12 generally includes a proximal end 26 and a distal end 28, whereby tubing 12 defines a fluid communication pathway extending therebetween. According to some embodiments, tubing 12 is comprised of conventional intravenous tubing used in conventional blood collection sets or infusion sets. In other embodiments, tubing 12 is comprised of relatively large bore tubing conventionally used in dialysis sets. It is contemplated that the structures and devices disclosed herein can be used in connection with tubing of any desirable type or dimension, including tubing conventionally used in various blood control devices, or other fluid collection, infusion, and/or transfer devices or sets.

Proximal fitting or connector 14 is generally comprised of plastic materials, such as polycarbonate, polypropylene, polyethylene, acrylic, polystyrene, ABS and/or other plastic materials, or combinations of plastic materials, having desirable properties. In some embodiments, proximal fitting 14 is molded unitarily. In other embodiments, proximal fitting 14 is assembled from discrete components. As illustrated in FIG. 1, proximal fitting 14 generally includes a proximal end 30 and a distal end 32, whereby proximal fitting 14 defines a fluid communication pathway extending therebetween. According to various embodiments, portions of the fluid communication pathway adjacent distal end 32 are configured to mate or telescope tightly over proximal end 26 of tubing 12. In this way, a fluid tight seal is formed between proximal fitting 14 and tubing 12, whereby a sealed fluid communication pathway extends therethrough. According to some embodiments, proximal end 30 of proximal fitting 14 defines a female luer connector configured to mate or connect with a corresponding male luer connector. This configuration allows a fluid, such a medication in liquid form, for example, to be infused into a patient via device 10.

In some embodiments, a male luer connector which corresponds to the female luer connector of proximal fitting 14 includes a proximal needle cannula that can be placed in communication with an evacuated tube. In other embodiments, the male luer connector includes an evacuated tube holder mounted to the male luer connector hub. In alternative embodiments, a male luer connector at the distal end of a conventional prior art syringe can be connected directly to proximal fitting 14 for infusing a fluid, such as a medication, into the patient via device 10. In some instances, a separate male luer cap can be provided for closing or otherwise sealing proximal fitting 14.

It is further contemplated that various fittings may be threadedly engaged with proximal fitting 14. In other embodiments, proximal connectors of other configurations similar to or dissimilar from connector 14 may be employed to achieve a particular objective. One example of an alternative fitting is a non-patient needle assembly with a male luer hub, a non-patient needle, and a non-patient sleeve mounted over the non-patient needle and secured to male luer hub. In such embodiments, the non-patient sleeve functions as a valve that permits multiple punctures of evacuated tubes or containers.

With continued reference to FIG. 1, needle assembly 16 generally includes a needle or needle cannula 34 and a needle hub 36. As illustrated, needle 34 has a proximal end 40 and a distal end 42, whereby needle 34 defines a fluid communication pathway extending therebetween. According to some embodiments, distal end 42 of needle 34 is beveled or chamfered to form a sharpened tip. In some embodiments, distal end 42 is formed having a single bevel or chamfer. In other embodiments, distal end 42 includes successive chamfered or beveled surfaces to facilitate insertion of needle 34 into a patient. According to some embodiments, needle 34 comprises a trocar having a sharpened 42. In some further embodiments, needle 34 comprises a guide for placing a catheter using device 10.

Turning briefly to FIG. 3B, according to some embodiments tip end 42 of needle 34 is configured to provide a consistent, smooth transition for less tissue trauma and greater patient comfort. As shown in FIG. 3B, for example, the design of tip 42 may include a multi-chamfered surface to provide a gradual transition. In some embodiments, tip end 42 of needle 34 includes a first chamfered surface 42A and a second chamfered surface 42B. According to some embodiments, first chamfered surface 42A includes a chamfer angle θ selected from about 1° to about 30°. In some embodiments, first chamfered surface 42A comprises a chamfer angel θ selected from about 10° to about 20°. In other embodiments, first chamfered surface 42A comprises a chamfer angle θ of about 15°.

Tip end 42 further includes a second chamfered surface 42B positioned between first chamfered surface 42A and the distal extremity of tip end 42. Second chamfered surface 42B includes a chamfer angle θ' selected from about 25° to about 45°. In some embodiments, second chamfered surface 42B comprises a chamfer angle θ' selected from about 30° to about 40°. In other embodiments, second chamfered surface 42B comprises a chamfer angle θ' of about 35°. According to various embodiments, chamfer angles θ and θ' of first and second chamfered surfaces 42A and 42B, respectively, progressively increase such that tip end 42 of needle 34 tapers inwardly. Thus, chamfer angle θ of first chamfered surface 42A is less than, or equal to, chamfer angle θ' of second chamfered surface 42B according to some embodiments.

In embodiments employing the devices and structures disclosed herein in connection with a transparent or translucent catheter coaxially disposed about needle 34, needle 34 is formed with a notch or opening 42C, i.e., a hole or opening in the sidewall adjacent to distal end 42 of needle 34. This configuration allows blood to flow into the open distal end of needle 34 and then out of notch 42C into the annular space between the catheter and needle 34. In embodiments having a transparent or translucent catheter, the user will be able to observe blood flashback promptly upon successful venipuncture.

According to some embodiments, needle 34 comprises of conventional needle used in conventional blood collection sets or infusion sets. In other embodiments, needle 34 comprises a relatively large gauge needle conventionally used in dialysis sets. It is contemplated that the structures and devices disclosed herein can be used in connection with a needle of any desirable type or dimension, including needles conventionally used in various blood control devices, or other fluid collection, infusion, and/or transfer devices or sets. For example, according to some embodiments device 10 is configured as a blood control dialysis set. In such embodiments, needle 34 generally comprises a large gauge needle, such as a 12g, 14g, 16g, 18g, etc. Other associated components are sized appropriately, including the use of large bore blood delivery tubes 12. In other embodiments, such as a standard blood collection set or an I.V. catheter, comparatively smaller gauge needles and tubing are employed in connection with the methods and structures disclosed herein.

Returning to FIGS. 1 and 2, needle hub 36 is generally comprised of plastic materials, such as polycarbonate, polypropylene, polyethylene, acrylic, polystyrene, ABS and/or other plastic materials, or combinations of plastic materials, having desirable properties. In some embodiments, needle hub 36 is molded unitarily. In other embodiments, needle hub 36 is assembled from discrete components. According to some embodiments, needle hub 36 is molded, formed, comprised, or assembled from transparent or translucent material(s) to enable a user's observation of fluid flowing through needle hub 36. Solvent bonding or plastic welding is contemplated in connection with the assembly or manufacture of various embodiments of needle hub 36.

As illustrated, needle hub 36 generally includes a proximal end 46 and a distal end 48, whereby needle hub 36 defines an internal stepped fluid communication pathway 50 (see FIGS. 12 and 13) extending therebetween. According to various embodiments, passage 50 adjacent proximal end 46 is dimensioned to compatibly couple with distal end 28 of tubing 12. In some embodiments, proximal end 46 of needle hub 36 comprises a male fitting configured for insertion within distal end 28 of tubing 12. In other embodiments, proximal end 46 of needle hub 36 comprises a female fitting configured to receive distal end 28 of tubing 12. In some instances, distal end 28 of tubing 12 mates with or is telescoped into passage 50 of needle hub 36 and is bonded in position to form a fluid tight seal between tubing 12 and needle hub 36. Similarly, according to various embodiments, passage 50 adjacent distal end 48 of needle hub 36 is dimensioned to compatibly receive proximal end 40 of needle 34 to form a fluid tight seal between needle hub 36 and needle 34.

Turning now to FIGS. 3A, 4, 5 and 6, and according to various embodiments, a portion of needle hub 36 adjacent distal end 48 defines a cylindrical tip 52. In some further embodiments a cylindrical spring mounting section 54 extends proximally from cylindrical tip 52. A larger diameter cylindrical flange 56 extends radially outwardly at the proximal end of spring mounting section 54. According to such embodiments, flange 56 defines a limit for proximal movement of spring 18 on needle hub 36 and a limit for distal movement of needle hub 36 relative to distal barrel 20. In some embodiments, flange 56 includes tabs for guiding movement of needle hub 36 within corresponding guide tracks or grooves formed in the barrel assembly comprised of distal and proximal barrels 20 and 22.

According to some embodiments, a resiliently deflectable actuator arm 60 is flexibly cantilevered to extend outwardly and distally from proximal end 46 of needle hub 36. This outward projection configuration enables actuator arm 60 to function as a key that maintains a specific rotational orientation of needle hub 36 relative to distal and proximal barrels 20 and 22. Additionally, actuator arm 60 and beveled tip 42 of needle 34 are axially aligned with one another according to some embodiments. Thus, in such instances, a plane passing through actuator arm 60 would also bisect the ellipse defined by beveled tip 42. In alternative embodiments, actuator arm 60 may be located on any side of needle hub 36.

According to some embodiments, actuator arm 60 includes a distal free end 62 (see FIG. 5) that is located proximally of flange 56. In such embodiments, flange 56 does not impede inward deflection of actuator arm 60. Portions of actuator arm 60 proximally of distal end 62 define an actuator button 64 that projects radially outwardly from actuator arm 60. In some further embodiments, the proximal end of actuator button 64 defines a locking edge 66 which is undercut relative to remaining portions of actuator arm 60 and oriented at an acute angle relative to the axis of needle hub 36. Some embodiments of needle hub 36 include a bottom stabilizing rib 67 (see FIG. 5), which rib extends axially along needle hub 36. More than one stabilizing rib may be used in accordance with various embodiments.

As discussed in greater detail below, in some embodiments button 64, other components of device 10, and/or a combination of the forgoing is/are configured so as to avoid inadvertent depression of button 64 and the associated premature deactivation of device 10. In other embodiments, as also discussed further below, other mechanisms are employed in connection with device 10 to avoid the inadvertent depression of button 64 and/or the premature deactivation of device 10.

With reference to FIGS. 3A and 4, according to some embodiments needle protector 38 is a rigid cylindrical tube that extends past the projecting length of needle 34 from distal end 72 (see FIG. 1) of distal barrel 20. As shown, in some embodiments, needle protector 38 attaches to needle hub 36 about cylindrical tip 52 and has a length that exceeds the projecting length of needle 34. In such embodiments, needle protector 38 defines an inside diameter approximately equal to the outside diameter of distal tip 52 of needle hub 36. Additionally, in some embodiments, needle protector 38 defines an outside diameter approximately equal to the outside diameter of spring mounting section 54 of needle hub 36. Thus, as shown most clearly in FIG. 4, needle protector 38 can be telescoped over needle 34 and frictionally retained on distal tip 52 of needle hub 36. Additionally, in this mounted condition, spring mounting section 54 of needle hub 36 and needle protector 38 define a continuous and substantially uniform outside diameter. In some alternative embodiments, needle protector 38 may be retained frictionally on distal end 72 (see FIG. 1) of distal barrel 20. According to some embodiments, needle protector 38 is not employed.

Returning briefly to FIG. 1, according to some embodiments spring 18 defines a helical coil with an inside diameter slightly greater than the outside diameter of needle protector 38 and/or spring mounting section 54 of needle hub 36. Additionally, in some implementations, the inside diameter of spring 18 is less than the outside diameter of flange 56 on needle hub 36. Thus, according to such embodiments, flange 56 defines a limit to the range of telescoping movement of spring 18 over needle assembly 16. According to various embodiments, the axial length of spring 18 is selected to conform with the desired range of movement of needle assembly 16 relative to distal and proximal barrels 20 and 22. In some instances, the axial length of spring 18 in its expanded condition exceeds the distance between distal tip 42 of needle 34 and flange 56 on needle hub 36.

In various implementations, distal barrel 20 includes opposite proximal and distal ends 70 and 72, whereby distal barrel 20 defines a passage 74 (see FIGS. 7 and 8) extending therebetween. In some embodiments, distal barrel 20 is generally comprised of plastic materials, such as polycarbonate, polypropylene, polyethylene, acrylic, polystyrene, ABS and/or other plastic materials, or combinations of plastic materials, having desirable properties. According to some embodiments, distal barrel 20 is molded unitarily. In other embodiments, however, distal barrel 20 is assembled from discrete components.

Figure 7:
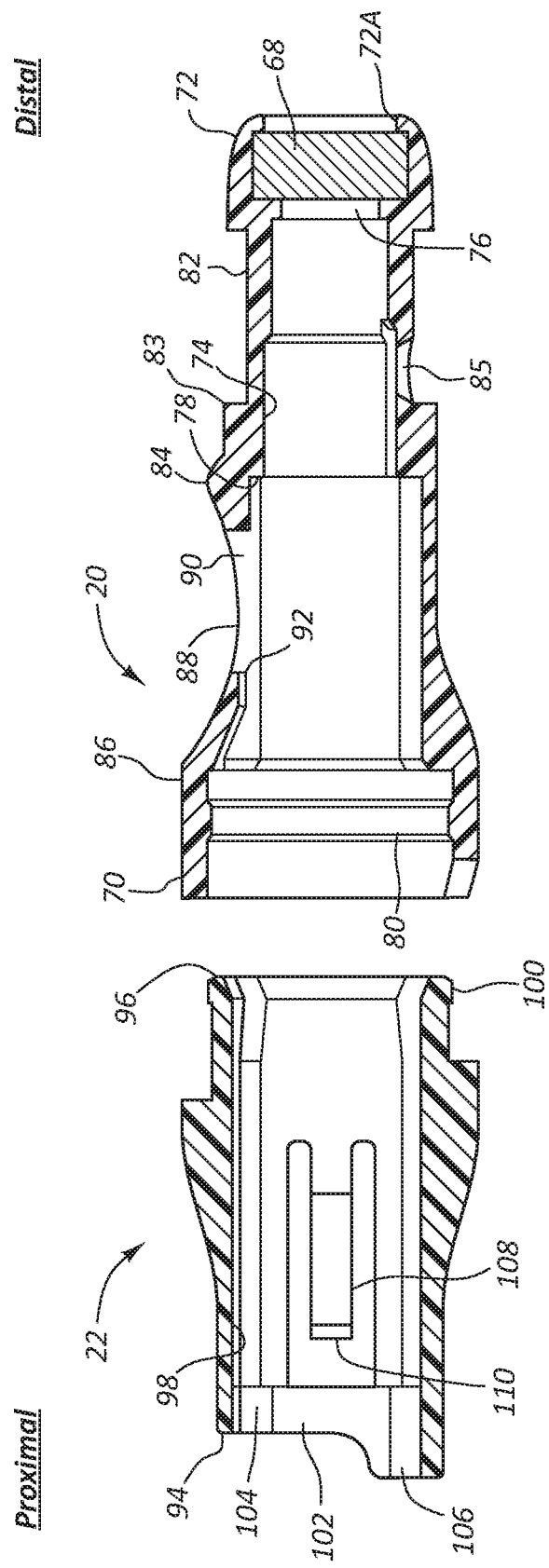
FIG. 7 is an exploded cross-sectional view of an assembly barrel.
Figure 8:
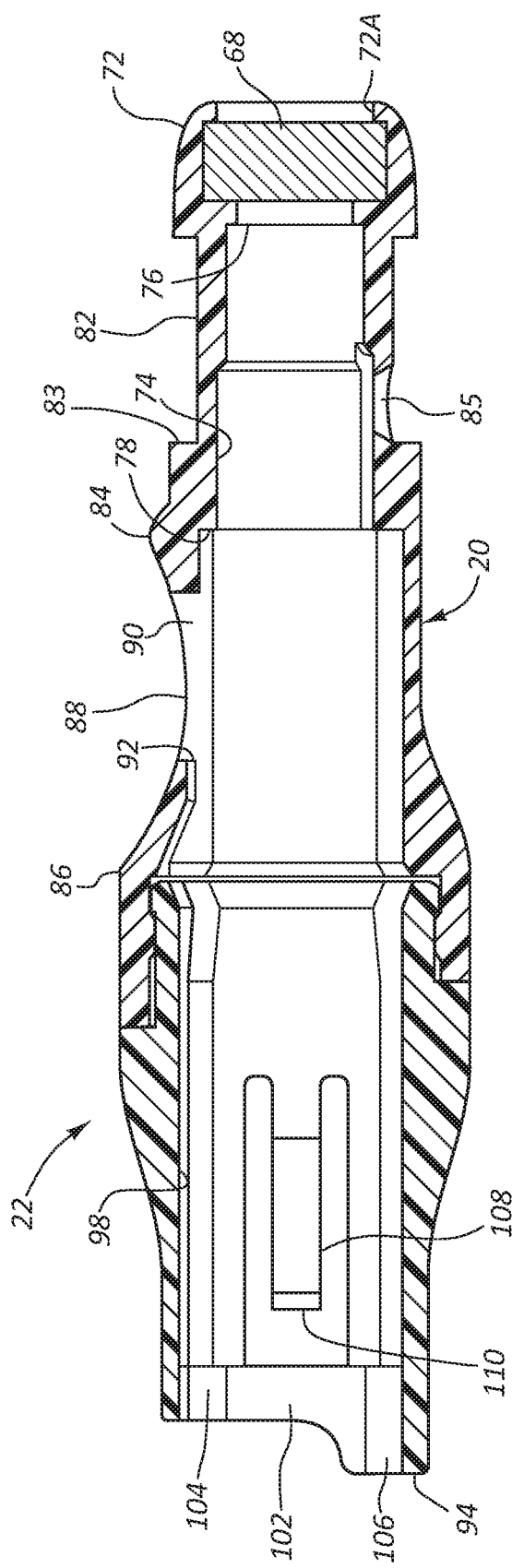
FIG. 8 is a longitudinal cross-sectional view of the barrel in its assembled condition.

With reference to FIGS. 7 and 8, according to some embodiments portions of passage 74 near distal end 72 define an inwardly extending annular distal flange 76 with an inside diameter less than the outside diameter of spring 18. Thus, in such implementations, distal flange 76 defines a distal stop or abutment for the distal end of spring 18, whereby spring 18 may be compressed within distal barrel 20. According to some additional embodiments, passage 74 further has an annular step 78 proximally of distal flange 76. In such embodiments, step 78 defines an inside diameter less than the outside diameter of flange 56 on needle hub 36. Thus, according to such embodiments, step 78 defines a fixed limit for the distal movement of needle hub 36 in distal barrel 20. According to various embodiments, step 78 is spaced from distal flange 76 by a distance substantially equal to the compressed length of spring 18. Thus, in such embodiments, the section of passage 74 between distal flange 76 and step 78 effectively defines a spring housing (see FIGS. 12 and 13). According to some embodiments, passage 74 is defined further by an annular locking rib 80 (see FIG. 7) near proximal end 70. Locking rib 80 permits locked engagement of distal and proximal barrels 20 and 22 as explained herein.

In some implementations, the outer circumferential surface of distal barrel 20 is defined by an annular wing-mounting undercut 82 near distal end 72. According to some further embodiments, annular undercut 82 is provided with projections or detents 83 for positioning wing attachment 24 in a fixed rotational orientation on distal barrel 20. In other embodiments, undercut 82 of distal barrel 20 has a dampening agent injection port 85 for injecting a dampening agent into passage 74. Port 85 is covered by wing attachment 24.

Figure 7A:
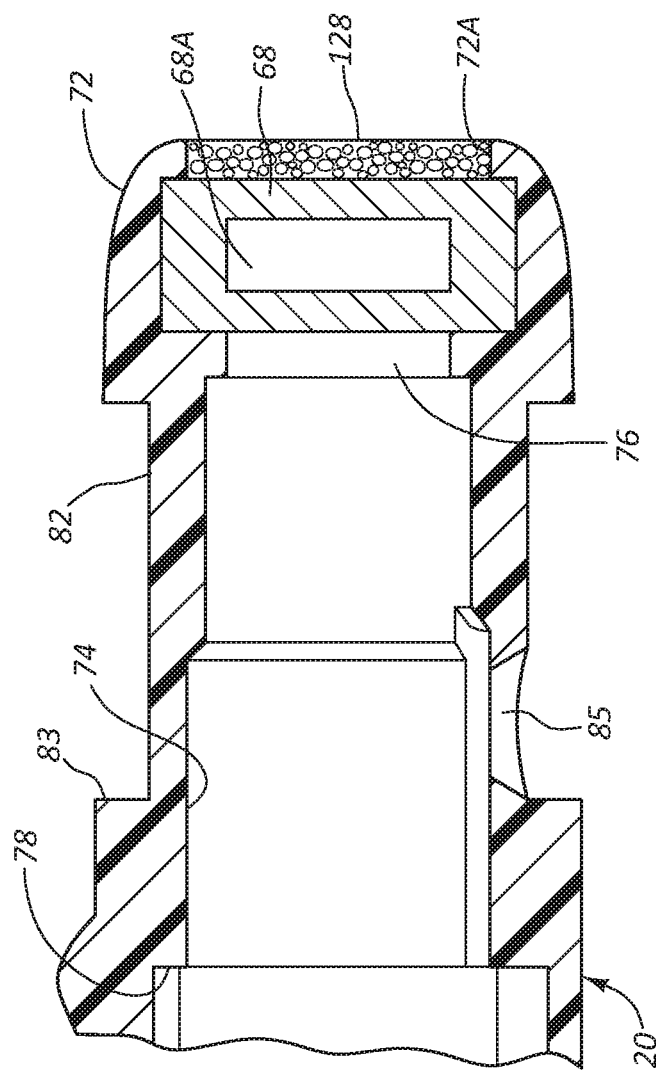
FIG. 7A is a blown up cross-sectional view of the distal end of the assembly barrel.

As shown in FIGS. 7A and 8, some embodiments include a septum 68 in proximity to the distal end of distal barrel 20. In such embodiments, the distal end of distal barrel 20 is sealed with septum 68 to ensure that fluid does not leak out of the distal end of distal barrel 20. In some embodiments, septum 68 is comprised of a single portion or otherwise formed unitarily and fitted into the distal end of distal barrel 20. In other embodiments, however, septum 68 is comprised of or otherwise formed having two or more portions. In such embodiments, one portion of septum 68 provides a primary seal while a second portion of septum 68 provides a secondary seal, and still a third portion of septum 68 provides a third seal. In various embodiments, septum 68 is pre-slit using various methods common to those of skill in the art. The slit formed within septum 68 accommodates or otherwise facilitates locating needle 34 there through.

According to some embodiments, suitable materials for septum 68 include a peroxide cured elastomer such as polyisoprene, silicone, and other like materials having a durometer in the range of 35-45 Shore A. In embodiments comprising septum 68 having two or more portions or components, each portion or component may be manufactured of the same material and/or have the same hardness. In other implementations, the discrete portions of a multi-part septum 68 can be manufactured out of different materials and/or have different durometers.

As illustrated in the various figures, septum 68 is retained in proximity to the distal end of distal barrel 20 via a septum housing according to various embodiments. For example, in some embodiments, the proximal face of septum 68 abuts the distal face of flange 76 while the distal face of septum 68 is retained by an annular distal flange 72A. In such embodiments, annular distal flange 72A extends over a portion of the surface area of the distal face of septum 68. In this configuration, septum 68 is fit within the cavity or housing defined between flanges 76 and 72A, whereby septum 68 is held in position in proximity to distal barrel 20. The proximity of septum 68 relative to distal barrel 20 is maintained as needle cannula 34 is located through the slit formed within septum 68 and subsequently withdrawn therefrom. In various embodiments, septum 68 is held in place and forms a fluid tight seal by various methods known in the art, such as through the use of an adhesive or by ultrasonic welding.

According to various embodiments, the septum housing defined by distal barrel 20 is configured to apply a compressive force to septum 68 to encourage a fluid tight seal. For example, in some embodiments, the outside diameter of septum 68 is between 1% and 10% larger than the inside diameter of the septum housing defined by distal barrel 20. In some embodiments, the outside diameter of septum 68 is at least 5% larger than the inside diameter of the septum housing defined by distal barrel 20. In this configuration, distal barrel 20 exerts a compressive radial force on the circumference of septum 68. The compressive radial force retains septum 68 in place and serves to seal septum 68 to prevent fluid from exiting therefrom.

Figure 12:
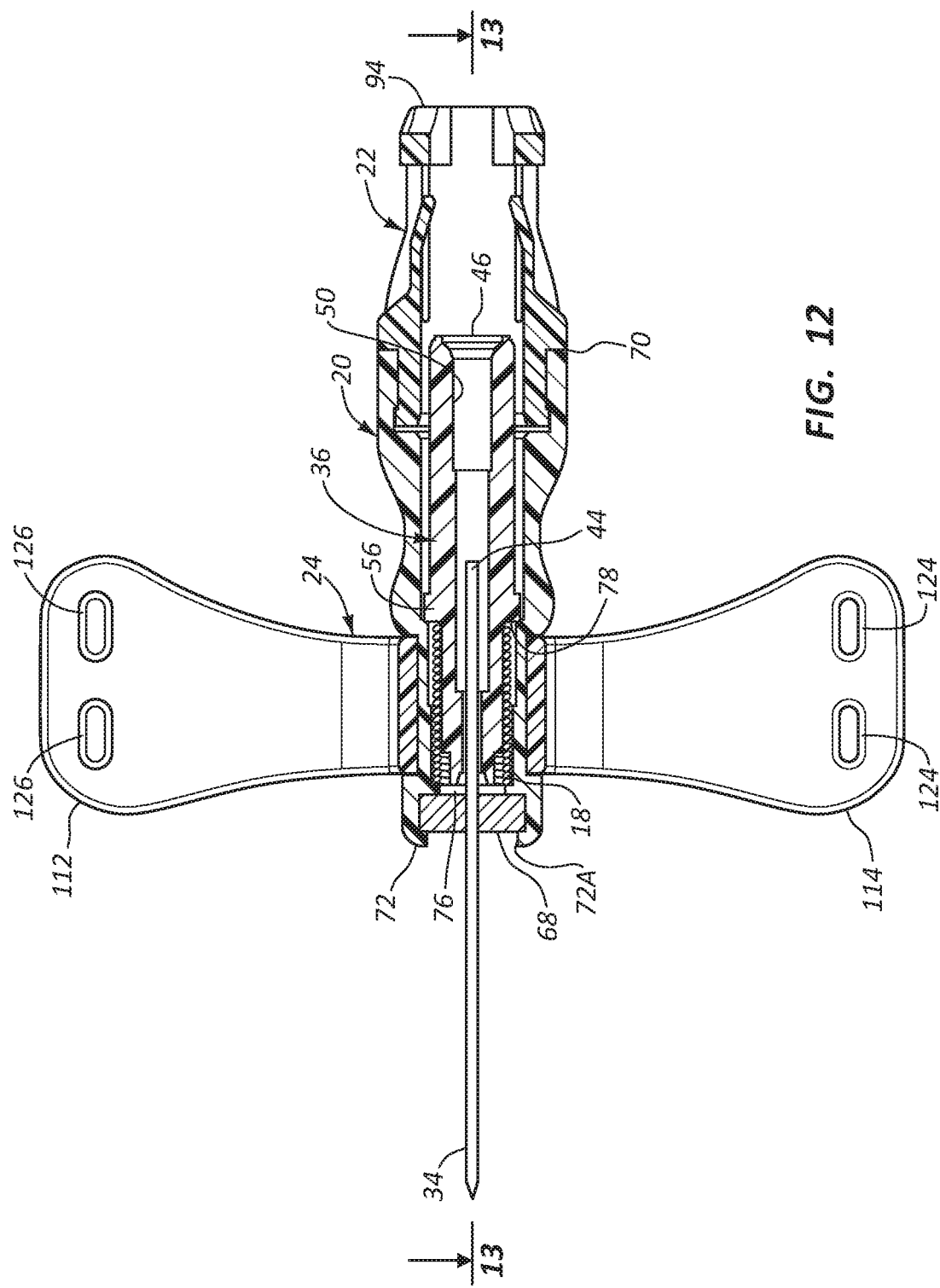
FIG. 12 is a cross-sectional view taken along line 12-12 in FIG. 11.
Figure 13:
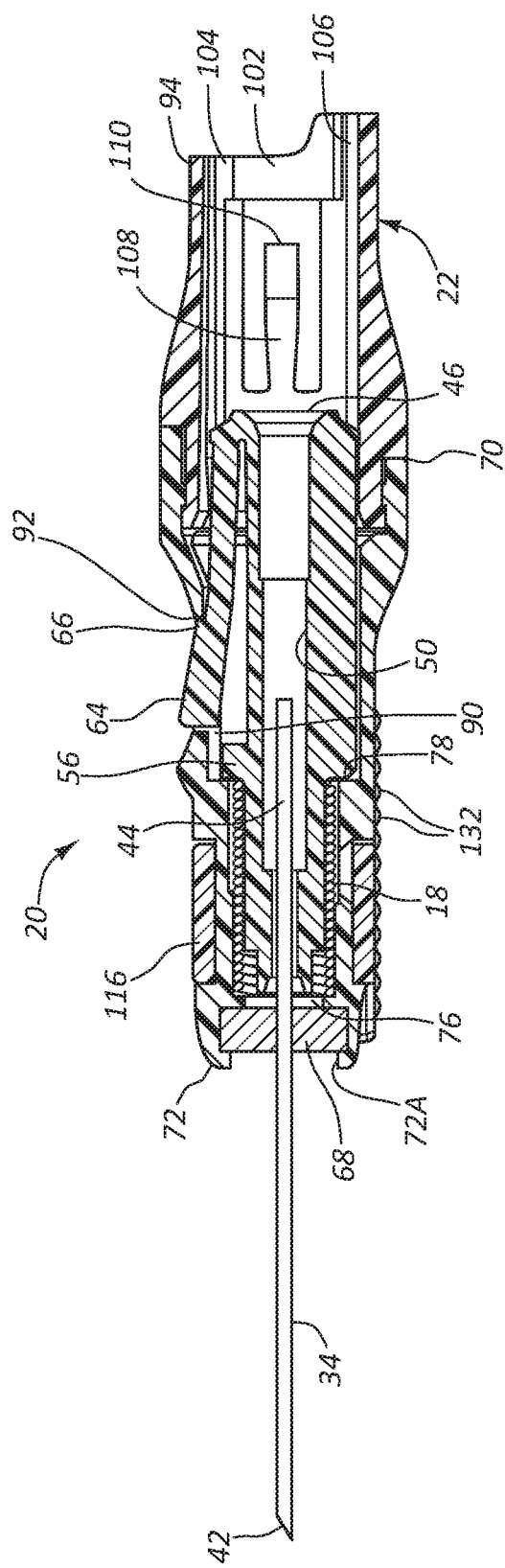
FIG. 13 is a cross-sectional view taken along line 13-13 in FIG. 12.
Figure 14:
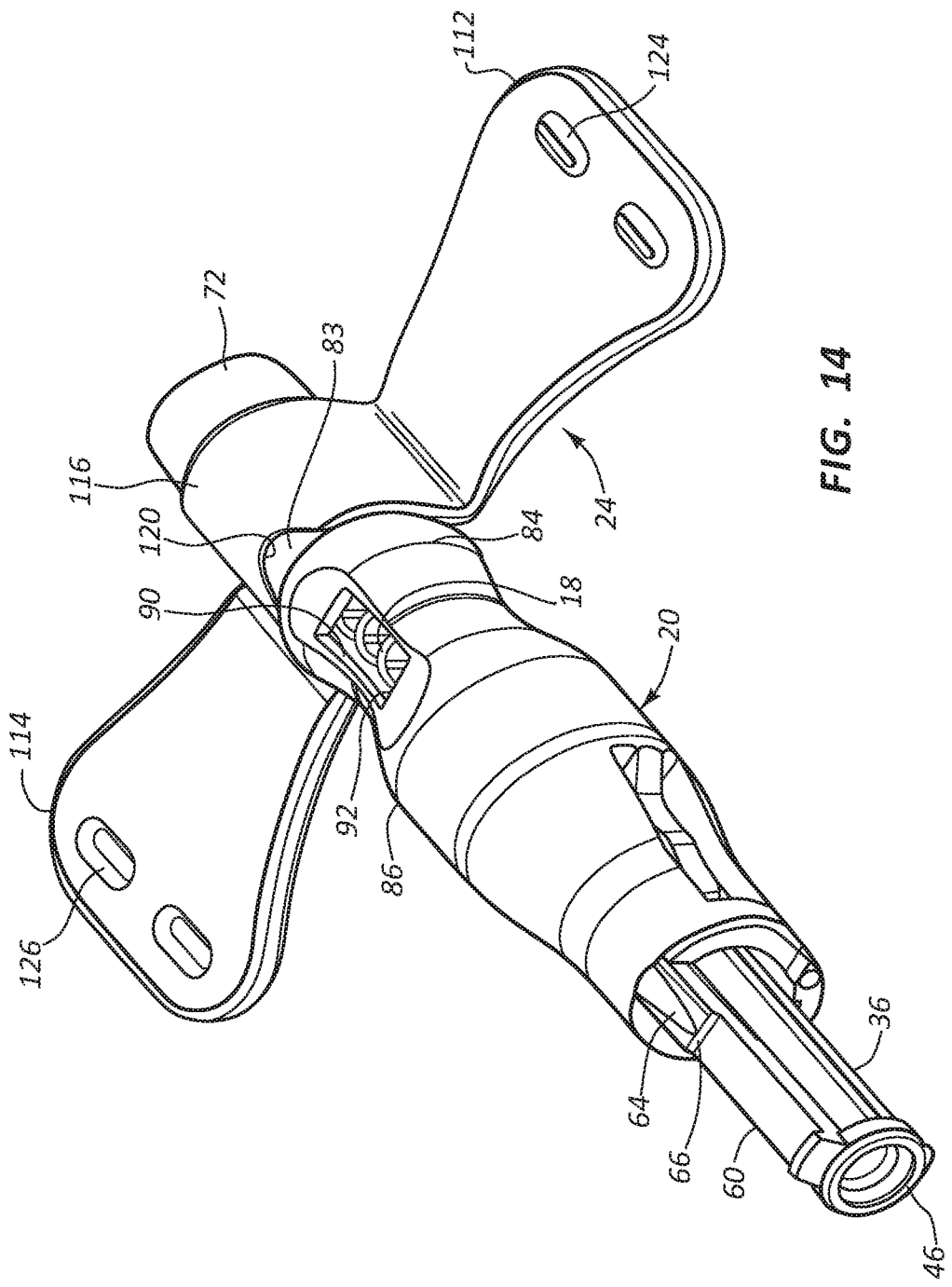
FIG. 14 is a perspective view similar to FIG. 10, but showing the needle assembly in its proximal, retracted, inactive, or deactivated position.
Figure 15:
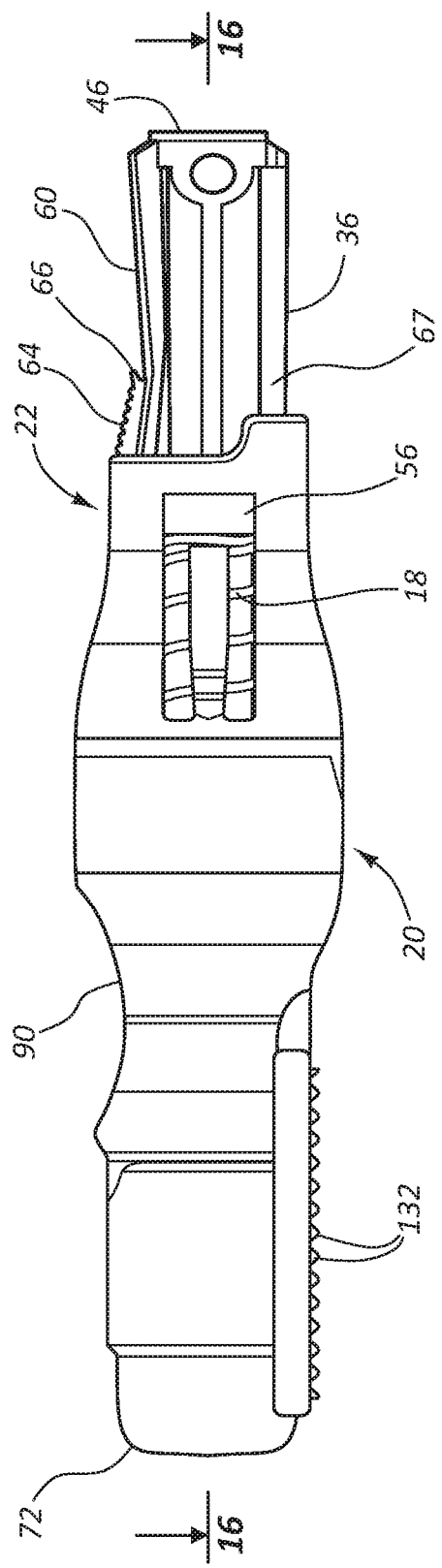
FIG. 15 is a side elevation view similar to FIG. 11 but showing the needle assembly in its proximal, retracted, inactive, or deactivated position.

As seen in various figures, including FIGS. 12 and 13, the open ends 70 and 72 of distal barrel 20 allow distal end 42 of needle 34 to extend through and distally past barrel 20 and septum 68 when device 10 is in an active position. In various embodiments, the radial compressive force discussed above helps to maintain a fluid tight seal after needle 34 has been retracted from septum 68 upon deactivation of device 10.

With brief reference to FIG. 7A, according to some embodiments, septum 68 defines an internal cavity or hollow interior portion 68A. In such embodiments, cavity 68A minimizes drag on needle 34 as it is retracted from septum 68. Such a configuration reduces splattering of residual fluid during retraction of needle 34. According to various embodiments, cavity 68A is sized to minimize drag without being too large. For example, in some embodiments, the cross-section of cavity 68A should closely approximate the cross-section of the largest bore needle 34 that would be used with device 10. In some further embodiments, the axial length of cavity 68A is between about 6 and 8 millimeters. In some instances, cavity 68A is filled with a material to prevent fluid from becoming trapped therein, such as a lubricious silicone liquid or gel or an antimicrobial solution.

Referring still to FIG. 7A, according to some embodiments, an absorbent material 128, such as a sponge, a pad, or some other wiping material, is disposed in proximity to septum 68. In various embodiments, material 128 comprises a non-woven or foam pad suitable for absorbing fluid. In such embodiments, material 128 soaks up, squeegees, or absorbs any residual fluid on the outside of needle 34 during retraction thereof. Such a configuration further reduces splattering of residual fluid during retraction of needle 34. Material 128 also prevents blood that would collect on the outside of septum 68 during retraction of needle 34 from dripping or otherwise leaking out of distal end 72 of distal barrel 20. In various embodiments, material 128 is a highly absorbent material capable of absorbing and positively retaining a quantity of residual fluid typically found on the outside of needle 34 during use of device 10 while in an active position.

Figure 16:
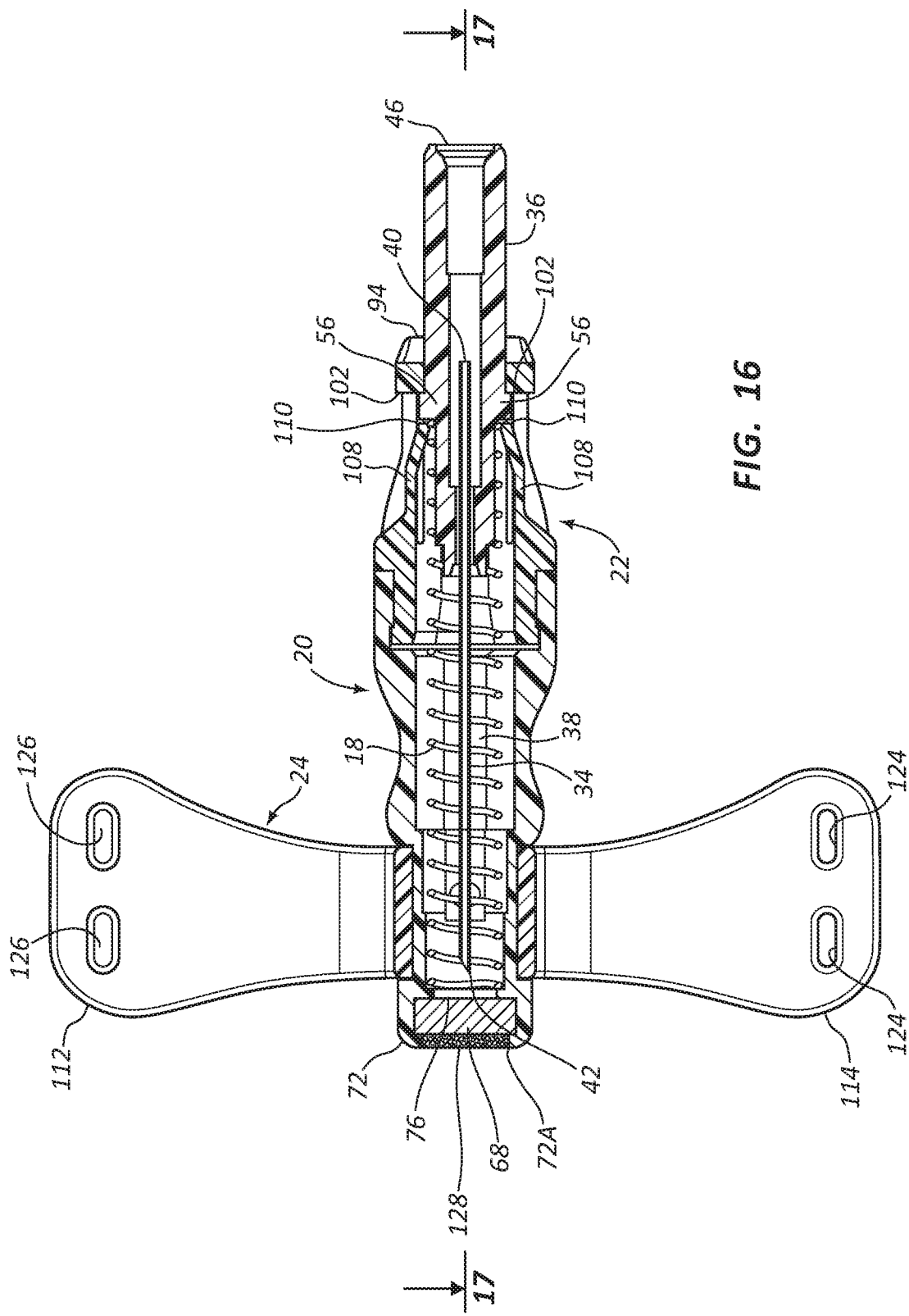
FIG. 16 is a cross-sectional view taken along line 16-16 in FIG. 15.
Figure 17:
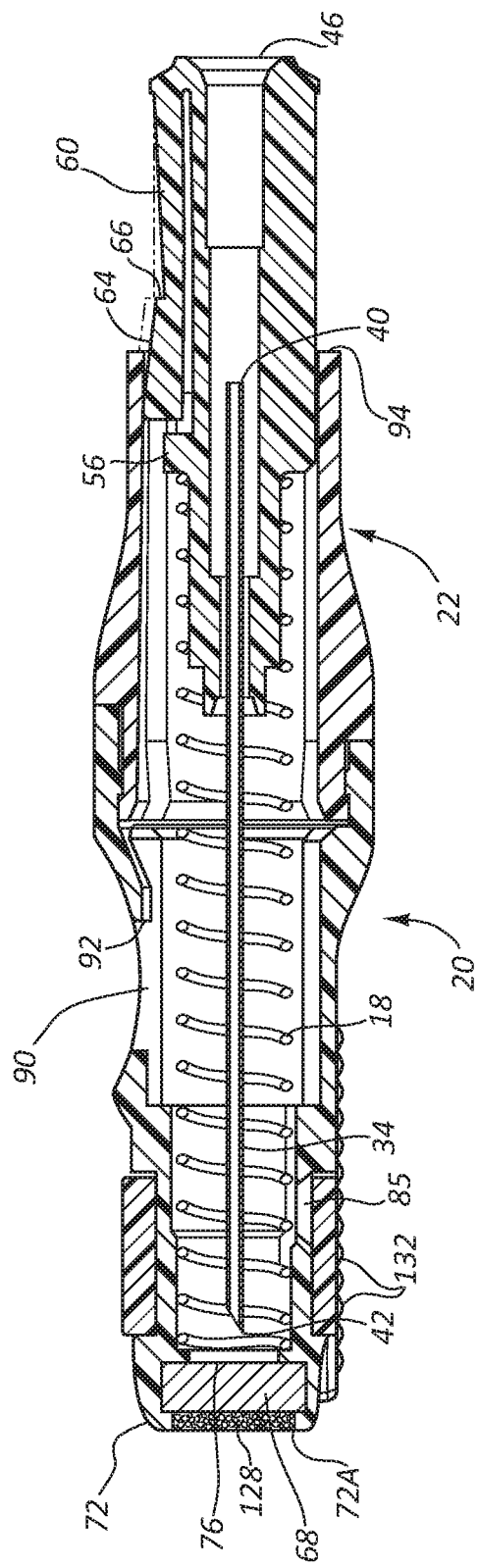
FIG. 17 is a cross-sectional view taken along line 17-17 in FIG. 16.

As shown in FIGS. 16 and 17, following withdrawal of needle cannula 34, when the distal end 42 thereof is proximal of septum 68, fluid, such as blood, cannot flow out of or otherwise exit from device 10 due to the fluid seal formed by septum 68. In some further embodiments, the retraction of needle 34 also allows absorbent material 128 to squeegee or wipe the outer surface of needle 34 and absorb any residual fluid that may be disposed thereon as needle 34 is withdrawn through the septum.

With returning reference to FIGS. 7 and 8, and according to various embodiments, some select portions of the outer surface of distal barrel 20 proximally of annular undercut 82 are flared outwardly. According to various embodiments, the outer circumferential surface is necked down to define a reduced diameter portion that extends through approximately 270° around the circumference of distal barrel 20. Thus, in some embodiments, distal barrel 20 includes a distal major diameter portion 84, a proximal major diameter portion 86, and a minor diameter portion 88 therebetween.

According to some further embodiments, minor diameter portion 88 of distal barrel 20 includes an actuating opening or barrel aperture 90 extending through distal barrel 20 and communicating with passage 74. In some embodiments, barrel aperture 90 is dimensioned to receive actuating button 64 and includes a locking edge 92 configured for locking engagement with locking edge 66 of actuating button 64. According to some embodiments, barrel aperture 90 is positioned angularly at a central location on minor diameter portion 88, and is aligned with projection 83 on undercut 82 to define a visually apparent top of distal barrel 20.

In some further embodiments, step 78 is spaced from barrel aperture 90 by a distance equal to or slightly greater than the axial distance between distal end 62 of actuator arm 60 and the distal face of flange 56. Thus, according to such embodiments, actuator button 64 is engaged in barrel aperture 90 when flange 56 of needle hub 36 abuts step 78 of distal barrel 20. Additionally, according to some embodiments, the internal cross-sectional dimension of passage 74 adjacent to and proximal of locking edge 92 is substantially equal to or slightly larger than the cross-sectional dimension of actuating arm 60 adjacent to and proximally of locking edge 66. Hence, in some embodiments, locked engagement is assured between locking edges 66 and 92 when needle hub 36 is moved distally in distal barrel 20 until flange 56 abuts step 78.

With brief reference back to FIGS. 1 and 2, and continued reference to FIGS. 7 and 8, according to various embodiments proximal barrel 22 also is generally a tubular structure with a proximal end 94, a distal end 96, and a passage 98 extending therebetween. In some embodiments, proximal barrel 22 is generally comprised of plastic materials, such as polycarbonate, polypropylene, polyethylene, acrylic, polystyrene, ABS and/or other plastic materials, or combinations of plastic materials, having desirable properties. According to various embodiments, proximal barrel 22 is molded unitarily while, in other embodiments, proximal barrel 22 is assembled from discrete components.

In some implementations, exterior portions of proximal barrel 22 adjacent distal end 96 define an annular locking bead or ring 100. In various embodiments, locking bead 100 is configured for snapped locking engagement with annular locking rib 80 in passage 74 of distal barrel 20. Such locking engagement serves to engage together distal and proximal barrels 20 and 22. According to some embodiments, the engagement of distal and proximal barrels 20 and 22 can be made more permanent by adhesive bonding, welding, or by increasing the interference between annular locking rib 80 and locking bead 100. In some alternative embodiments, however, distal barrel 20 and proximal barrel 22 are connected by threaded engagement where one of distal and proximal barrels 20 and 22 has external threads and the other of distal and proximal barrels 20 and 22 has internal threads. According to such embodiments, thread pitch and location are chosen to enable alignment of top and bottom axially extending channels 104 and 106. In some embodiments, the barrel assembly includes additional channels or guide tracks configured to engage guide tabs located adjacent flange 56 included on needle hub 36. In such embodiments, the interaction of guide tabs on flange 56 and corresponding guide tracks or channels formed in the barrel assembly facilitate the guided proximal movement of needle hub 36 during retraction or deactivation of device 10.

According to various embodiments, proximal portions of passage 98 through proximal barrel 22 are characterized by an inwardly extending proximal annular flange 102. Proximal flange 102 has an inside diameter less than the outside diameter of flange 56 on needle hub 36. Thus, according to some implementations, proximal flange 102 limits proximal movement of needle hub 36 in proximal barrel 22 once distal and proximal barrels 20 and 22 are engaged with one another.

As illustrated in FIG. 7, according to some embodiments passage 98 of proximal barrel 22 is characterized further by top and bottom axially extending channels 104 and 106, respectively. According to such embodiments, top channel 104 is aligned with barrel aperture 90 and is dimensioned to slidably receive actuating arm 60 of needle hub 36. Similarly, bottom channel 106 is dimensioned to slidably receive needle hub 36. In some embodiments, bottom channel 106 is configured to receive bottom stabilizing rib 67 of needle hub 36.

According to some embodiments, portions of proximal barrel 22 surrounding bottom channel 106 project proximally beyond portions of proximal barrel 22 surrounding top channel 104. In such configurations, a greater axial length is provided for slidably receiving and supporting bottom stabilizing rib 67 of needle hub 36. According to some embodiments, additional support for bottom stabilizing rib 67 achieves a more desirable bearing ratio between the cross-sectional and axial dimensions for slidable engagement between needle hub 36 and barrels 20 and 22. Thus, a more precise axial movement is achieved with less transverse shifting of needle hub 36. The more precise axial movement enabled by the proximal extension surrounding bottom channel 106 reduces splattering of residual fluid in needle 34 during retraction thereof.

In some further embodiments, proximal barrel 22 includes resiliently deflectable locking fingers 108. Locking fingers 108 are cantilevered distally and inwardly from opposing locations on proximal barrel 22. Locking fingers 108 are also spaced from top and bottom channels 104 and 106 by approximately 90° according to some embodiments. Thus, each locking finger 108 includes a proximal end 110 that is spaced from proximal stop or retention flange 102 by a distance equal to or slightly greater than the axial thickness of flange 56 on needle hub 36. Hence, according to such embodiments, flange 56 can be trapped between the distal surface of stop flange 102 and locking figures 108 as explained below. According to various embodiments, proximal ends 110 of locking figures 108 are spaced from one another by a distance less than the diameter of flange 56 on needle hub 36.

According to various embodiments, the barrel assembly comprised of distal barrel 20 and proximal barrel 22 is molded, formed, comprised, or assembled from transparent or translucent material(s) to enable observation of blood or other fluid flowing through the barrel assembly. Solvent bonding or plastic welding is contemplated in connection with the assembly or manufacture of various embodiments of the barrel assembly.

Figure 9:
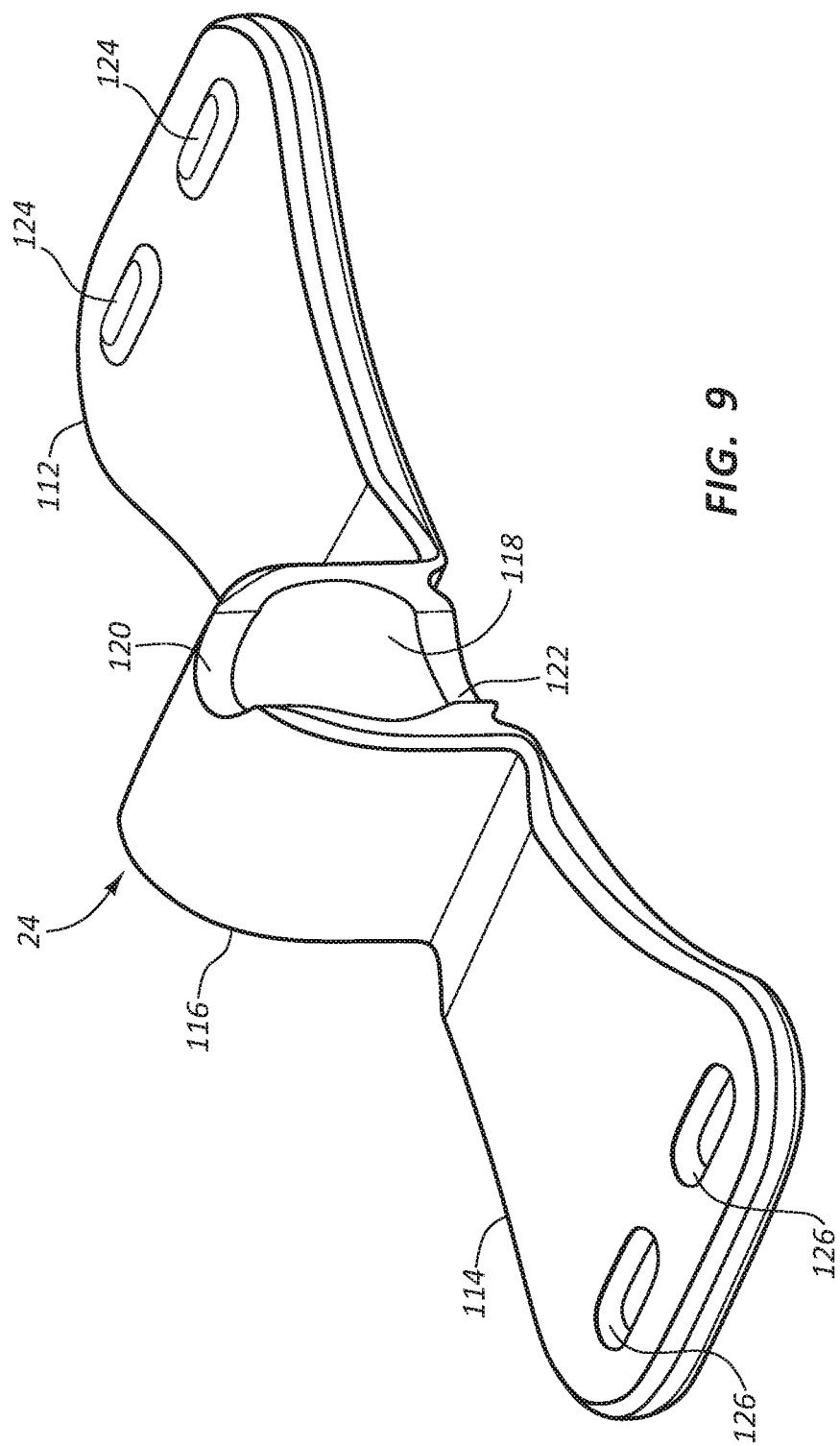
FIG. 9 is a perspective view of one embodiment of a wing attachment.

With brief reference back to FIGS. 1 and 2, and specific reference now to FIGS. 9, 10 and 11, wing attachment 24 will be discussed in greater detail. According to various embodiments, wing attachment 24 is molded unitarily from an elastic material such as polyolefin, polyvinyl chloride, or other such elastomeric polymers having flexible or semi-flexible properties. According to other embodiments, however, wing attachment 24 is molded of comparatively semi-rigid materials having a desirable amount of shape memory. In still other embodiments, wing attachment 24 is generally molded of elastomeric polymers formed around a comparatively semi-rigid structural skeleton. As shown, wing attachment 24 generally includes flexible opposing side panels 112 and 114 and a mount 116. In some embodiments, as depicted by way of example, mount 116 is tubular in configuration. In other embodiments, however, mount 116 forms an upside down "u" shape traversing approximately 270° and having an opening at the bottom thereof.

In various embodiments, mount 116 includes an interior passage 118 that is dimensioned for snug engagement over and/or around undercut 82 on distal barrel 20. In some additional embodiments, mount 116 is formed with top and bottom notches 120 and 122. Notches 120 and 122 are dimensioned to engage with detents 83 on distal barrel 20 to ensure a preferred rotational orientation between wing attachment 24 and distal barrel 20. According to various alternative embodiments, notches 120 and 122 are symmetrical about a plane that is perpendicular to panels 112 and 114.

According to some embodiments, opposing panels 112 and 114 are molded with a top surface that is relatively smooth. In some embodiments, the top surface of one of panel 112 or 114 includes a pair of arcuate projections 124 at portions remote from mount 116. Conversely, according to some embodiments, the top surface of the other of panel 112 or 114 includes a pair of arcuate recesses 126 that are dimensioned to receive projections 124 when panels 112 and 114 are folded so that the top surfaces thereof are in face-to-face engagement with one another. According to such embodiments, the inter-engagement of projections 124 with recesses 126 ensures that folded panels 112 and 114 function as a handle without slipping relative to one another when folded and engaged. According to additional embodiments, as seen in FIG. 11, the bottom surfaces of panels 112 and 114, respectively, are provided with a plurality of tactile bumps 132. In such embodiments, bumps 132 facilitate a user's grip of folded panels 112 and 114 between a thumb and forefinger of the user. According to the foregoing embodiments, and as depicted in the various figures, the hinged movement described with respect to panels 112 and 114 about mount 116 is facilitated by thinned regions (e.g., FIG. 9) at the connection of panels 112 and 114 with mount 116.

According to various alternative embodiments, the color of wing attachment 24 is coordinated with, or otherwise designates, the gauge of needle 34. Alternate embodiments where wing attachment 24 has only one side panel 112 or 114 are contemplated to provide an alternate means to manipulate the needle assembly by the user.

With general reference to FIG. 1 and specific reference to FIGS. 12 and 13, according to some embodiments, device 10 is assembled by axially coupling proximal end 40 of needle 34 with passage 50 adjacent distal end 48 of needle hub 36. Needle 34 may be secured in this position by an adhesive, such as a heat curable or ultraviolet cured epoxy. Similar securing methods or means common to those of skill in the art are also contemplated. According to some embodiments, the bevel or multiple chamfers that define distal tip 42 of needle 34 require a specific orientation. As shown in the various figures, for example, in some embodiments, needle cannula 34 is oriented such that the bevel at distal end 42 of needle 34, wing attachment 24, and actuator arm 60 of needle hub 36 are symmetrical about a common plane. In some further embodiments, the orientation of wing attachment 24 relative to distal end 42 of needle 34 is guaranteed by the relative orientation of actuator arm 60 and needle hub 36 with respect to distal and proximal barrels 20 and 22. The method of assembly continues, according to some embodiments, as needle assembly 16 is completed by telescoping protector 38 over needle 34 sufficiently for frictional engagement on distal tip 52 (see FIG. 3A) of needle hub 36. In various alternative embodiments, protector 38 can be telescoped over needle cannula 34 by fictional engagement with distal barrel 20. In some instances, protector 38 is not telescoped over needle cannula 34 until after needle cannula 34 has been located through septum 68 as discussed below.

According to various embodiments, the assembly of device 10 continues as distal end 28 of tubing 12 is coupled with proximal end 46 of needle hub 36. In some implementations, tubing 12 is secured in this position by solvent bonding, adhesive bonding, or welding. Other methods of securing suitable tubing common to those of skill in the art are also contemplated.

With respect to some embodiments, assembly continues by telescoping spring 18 over needle protector 38 and/or over spring mounting section 54 of needle hub 36. According to some embodiments, needle assembly 16 and spring 18 are then aligned and telescoped in a distal direction into distal barrel 20. In embodiments comprising septum 68, needle assembly 16 and spring 18 are aligned and telescoped into distal barrel 20 such that needle 34 passes through a preformed slit in septum 68 before needle protector 38 is coaxially disposed over needle 34. For various embodiments, the above-described insertion requires that actuator arm 60 and stabilizing rib 67 (e.g., FIG. 5) be aligned with channels 104 and 106 (e.g., FIG. 10). Movement of needle hub 36 into distal barrel 20 causes needle 34 to advance through and beyond septum 68 and distal end 72 of distal barrel 20 whereupon needle protector 38 can be coaxially disposed over needle 34. Additionally, according to some embodiments, actuator arm 60 (e.g., FIG. 5) is depressed sufficiently to clear portions of passage 74 immediately proximally of barrel aperture 90 during installation and assembly (e.g., FIG. 7).

As illustrated in FIGS. 12 and 13, the distal movement described above causes spring 18 to collapse between distal flange 76 on distal barrel 20 and flange 56 on needle hub 36. According to various embodiments, the method continues as flange 56 of needle hub 36 approaches step 78 of distal barrel 20 and actuator button 64 aligns with barrel aperture 90. As seen in FIG. 13, as actuator arm 60 fully aligns with barrel aperture 90, actuator arm 60 resiliently returns toward an undeflected condition and locking edge 66 of actuator button 64 engages locking edge 92 of barrel aperture 90. As a result of the interaction of locking edges 66 and 92 and the resilient biased orientation of actuator arm 60, needle assembly 16 is locked in its distal position in distal barrel 20 with spring 18 secured in a compressed condition with significant stored energy. According to various embodiments, when needle assembly 16 is locked in its distal position and needle protector 38 is removed, device 10 is active or otherwise configured for placement of device 10 into fluid communication with a patient via exposed needle 34.

As shown in various Figures, assembly of device 10 continues as wing attachment 24 is mounted over distal end 72 of distal barrel 20. According to some embodiments, notches 120 and 122 of wing attachment 24 are aligned with detents 83 on distal barrel 20 (e.g., FIGS. 10 and 11). In some further embodiments, a snug fit between mount 116 of wing attachment 24 and wing-mounting undercut 82 of distal barrel 20 is achieved via the interaction of detents 83 and notches 120 and 122. This configuration prevents rotation of wing attachment 24 relative to distal barrel 20. In its mounted condition, panels 112 and 114 of wing attachment 24 define a plane extending substantially normal to the plane of symmetry defined by the bevel at distal tip 42 of needle 34 and actuator arm 60 of needle hub 36.

Returning to FIG. 1, according to various embodiments, assembly of device 10 continues by threading proximal end 26 of tubing 12 through proximal barrel 22. Proximal barrel 22 is moved distally along the length of tubing 12 until distal end 96 of proximal barrel 22 lockedly engages proximal end 70 of distal barrel 20 via locking rib 80 and locking ring 100 (e.g., FIG. 7). The method continues, according to various embodiments, as fitting 14 is secured to proximal end 26 of tubing 12. Fitting 14 can be secured to proximal end 26 of tubing 12 by any method common to those of skill in the art.

In embodiments in which a viscous dampening agent is utilized via port 85, passage 74 of distal barrel 20, the spring mounting section 54 of needle hub 36, and the distal surface of flange 56 on needle hub 36 define a chamber that constrains the location of the dampening agent or otherwise defines a cavity to be filed with the dampening agent. Alternatively, another silicone part could be used as a bumper. As mentioned above, in such embodiments, an injection port 85 located within the sidewall of distal barrel 20 is provided for dispensing the viscous dampening agent into the dampening agent chamber. In some embodiments, the dampening agent can be injected through a dispensing cannula that has a distal end shaped to fit within injection port 85. In other embodiments it is also contemplated that the dampening agent can be applied to passage 74, spring 18, needle hub 36, or any of the three components prior to assembly to produce an alteration to retraction speed or velocity when needle assembly 16 is retracted following use of device 10.

According to some embodiments, the viscous dampening agent may be a silicone that functions to dampen the velocity of needle hub 36 relative to distal barrel 20 and proximal barrel 22. In such embodiments, the viscous dampening agent creates a resistance to slow the retraction of needle hub 36 and needle 34. In some embodiments a suitable dampening agent is a thixotropic gel, similar to the type of gel used as a separator gel in blood collection tubes. Utilization of a thixotropic gel as a dampening agent provides unique properties relative to spring 18. In particular, thixotropic gel exhibits the ability to temporarily and elastically bond adjacent coils of spring 18 together. Initiation of retraction releases the stored energy of spring 18, and permits spring 18 to expand. Nevertheless, the thixotropic gel creates resistance similar to silicone, and hence dampens the velocity of needle hub 36 and needle 34 during the retraction process. However, unlike conventional silicone, the temporary bonding between adjacent coils achieved by the thixotropic gel provides a slower initial acceleration. In such embodiments, the slower initial acceleration results in a reduction in splatter during retraction of needle assembly 16.

According to some embodiments, injection port 85 is positioned on undercut 82 (see FIGS. 7 and 8) and is sealed by placing wing attachment 24 on and covering injection port 85, thereby constraining the dampening agent to that portion of spring 18 near injection port 85. In alternative embodiments, it is understood that a dampening agent can be located on surfaces in slidable engagement between needle hub 36 and distal and proximal barrels 20 and 22. In such embodiments, the dampening agent produces a viscous shearing boundary layer that alters the velocity and acceleration of needle hub 36 during retraction thereof.

With reference now to FIGS. 14 through 17, and continued general reference to FIGS. 1 and 2, methods of using device 10 according to various embodiments are described in further detail. In some embodiments, for example, device 10 is used by folding panels 112 and 114 of wing attachment 24 toward one another and into face-to-face engagement so that projections 124 on the upper surface of one of panel 112 and/or 114 are received in recesses 126 on the upper surface of the other one of panel 112 and/or 114. This configuration prevents shifting of panels 112 and 114 during use of device 10. In such embodiments, tactile bumps 132 (e.g., FIG. 15) on the bottom surfaces of panels 112 and 114, respectively, facilitate a user's secure grip of device 10 via pinching panels 112 and 114 between the user's thumb and forefinger.

According to various embodiments, the method of using device 10 continues as needle protector 38 is separated from frictional engagement with either needle hub 36 or distal barrel 20 in order to expose needle 34.

In some embodiments, the plane defined by the abutting surfaces of panels 112 and 114 of wing attachment 24 will lie on the plane of symmetry of beveled distal tip 42 of needle 34. Such a configuration permits the user, such as a health care worker, a clinician, a nurse, a health care technician, or any other or equivalent health care professional, to guide beveled distal tip 42 of needle 34 into a target location on a patient. According to various embodiments, the method continues as the user employs proximal fitting 14 at proximal end 26 of tubing 12 to connect device 10 to other medical equipment or devices, such as an evacuated container, a source of fluid that will be infused into the patient, a dialysis or blood cleaning/filtering machine, an I.V. tube or bag, or other medical equipment or devices common to those of skill in the art.

According to certain implementations, upon completion of the associated medical procedure being performed, the health care worker deactivates device 10 by depressing actuator button 64. The depression of actuator button 64 enables needle assembly 16 to be retracted, whereby the barrel assembly comprised of distal and proximal barrels 20 and 22 entirely encloses needle 34 once needle assembly 16 is fully retracted. In embodiments comprising septum 68 and or absorbent material 128, the barrel assembly also contains any residual blood or other fluid inside device 10. In this configuration, once deactivated, device 10 protects users against needle stick injuries as well as potential blood borne pathogens.

As mentioned briefly above, according to some embodiments, actuator button 64 lies within the reduced cross-section or minor diameter portion 88 of distal barrel 20, and hence is not susceptible to inadvertent actuation or depression. However, in some embodiments, the configuration of minor diameter portion 88 is dimensioned to receive a tip of a user's finger, such as a user's forefinger, that is intentionally directed toward actuator button 64. In some further embodiments, the necked-down shape of distal barrel 20 adjacent barrel aperture 90 provides a clear visual cue for the intended location of manual force for depressing actuator button 64. In some alternative embodiments, actuator button 64 comprises a low profile such that deliberate and targeted effort is necessary to effectively depress the same. Additional embodiments configured to reduce or prevent incidents of inadvertent actuation or depression of actuator button 64 are discussed in greater detail below.

According to some embodiments, in operation, inwardly directed forces on actuator button 64 cause locking edge 66 of actuator button 64 to disengage from locking edge 92 of barrel aperture 90. In such embodiments, spring 18 is permitted to expand releasing the energy stored therein as locking edges 66 and 92 are disengaged. The disengagement of locking edges 66 and 92 results in the retraction of needle assembly 16. As most clearly seen in FIG. 16, in some implementations, the proximal movement of needle assembly 16 terminates when flange 56 abuts proximal stop flange 102 of proximal barrel 22 and the sharp tip 42 of needle 34 is proximal of septum 68. In this position, the entirety of needle 34 is disposed safely within distal and proximal barrels 20 and 22 to prevent needle stick injuries. Likewise, in this position, septum 68 seals device 10 so as to contain any residual blood, prevent the user from being exposed to blood borne pathogens, and prevent blood from exiting device 10.

Figure 10:
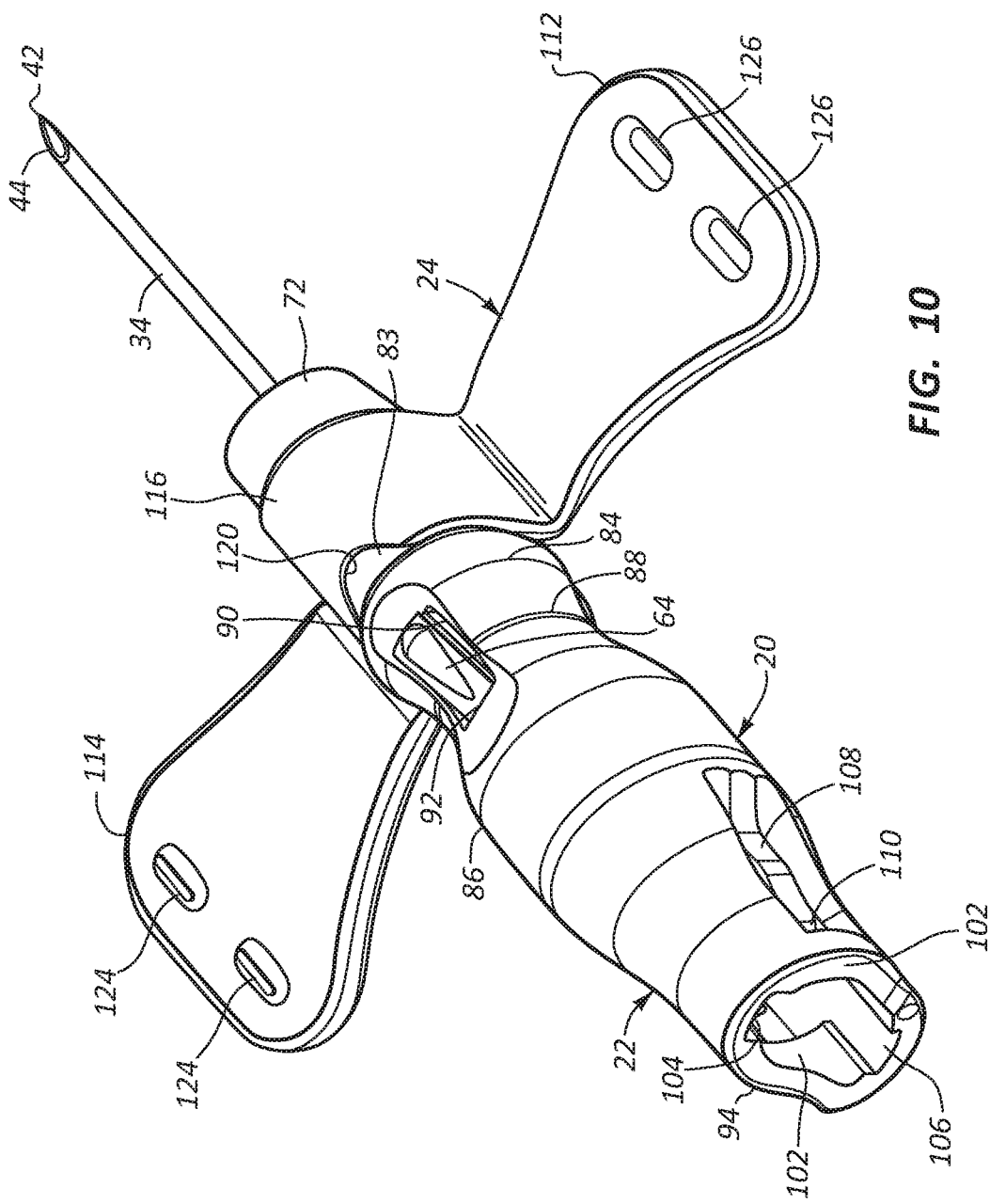
FIG. 10 is a perspective view of the retractable needle apparatus of some embodiments of the fluid collection or infusion device or set with the needle assembly in its distal, extended, or active position.
Figure 11:
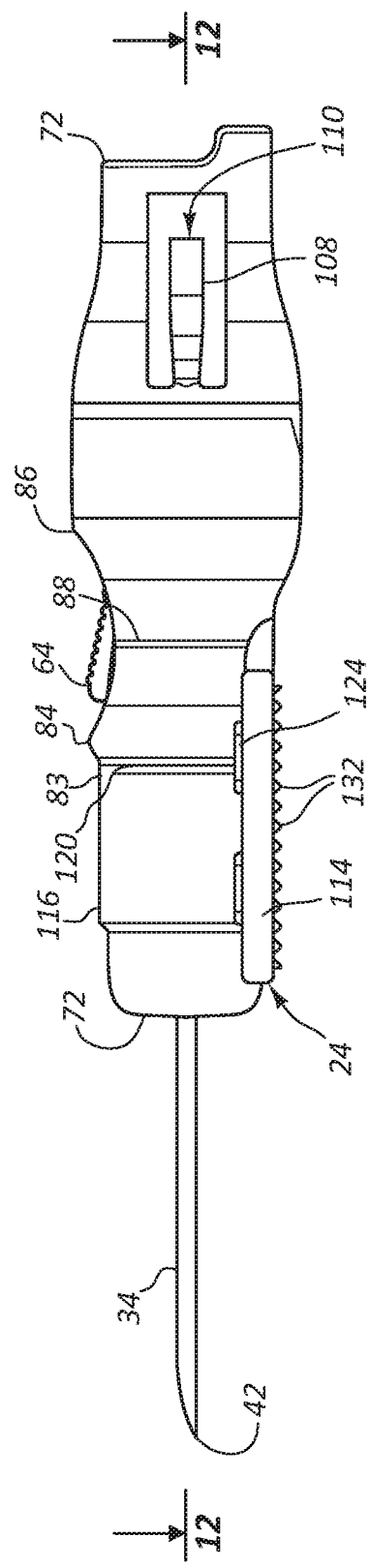
FIG. 11 is a side elevation view of the retractable needle apparatus shown in FIG. 10.

According to some further embodiments, the retraction of needle assembly 16 is guided axially by engagement of bottom stabilizing rib 67 in bottom channel 106 (e.g., FIG. 10). In various additional embodiments, actuator button 64 travels in top channel 104 (e.g., FIG. 10) and biases needle assembly 16 toward bottom channel 106 during retraction of needle assembly 16, including portions of bottom channel 106 in proximal extension of proximal barrel 22. Thus, according to some embodiments, an effective bearing ratio is maintained to achieve axial movement while reducing incidents, or the probability, of fluid splatter as needle 34 is accelerated proximally under the force of spring 18.

According to various embodiments, as flange 56 of needle hub 36 approaches proximal stop 102 of proximal barrel 22, flange 56 engages locking fingers 108. In such embodiments, the rearward movement of flange 56 causes a temporary outward deflection of locking fingers 108 until flange 56 moves proximally beyond the proximal ends 110 of locking fingers 108. As shown in FIG. 16, the method of deactivating device 10 continues as needle assembly is further retracted until flange 56 abuts proximal stop 102, at which point locking fingers 108 resiliently return toward an undeflected condition and engage the distal face of flange 56. Hence, according to some embodiments, a return movement of needle assembly 16 is prevented. Thus, according to some embodiments, the interaction of locking fingers 108 of proximal barrel 22, flange 56 of needle hub 36, and spring 18 restrains needle assembly 16 against subsequent distal movement following deactivation of device 10. In this way, device 10 is restrained against inadvertent reactivation. In some further embodiments, the inwardly aligned orientation of locking fingers 108 substantially impedes any intentional outward deflection of locking fingers 108 that would permit a re-exposure or re-activation of needle 34. Thus, in some implementations, reuse of needle 34 is prevented following deactivation of device 10 or can be achieved only by a destruction of the locking fingers in proximal barrel 22.

Figure 18A:
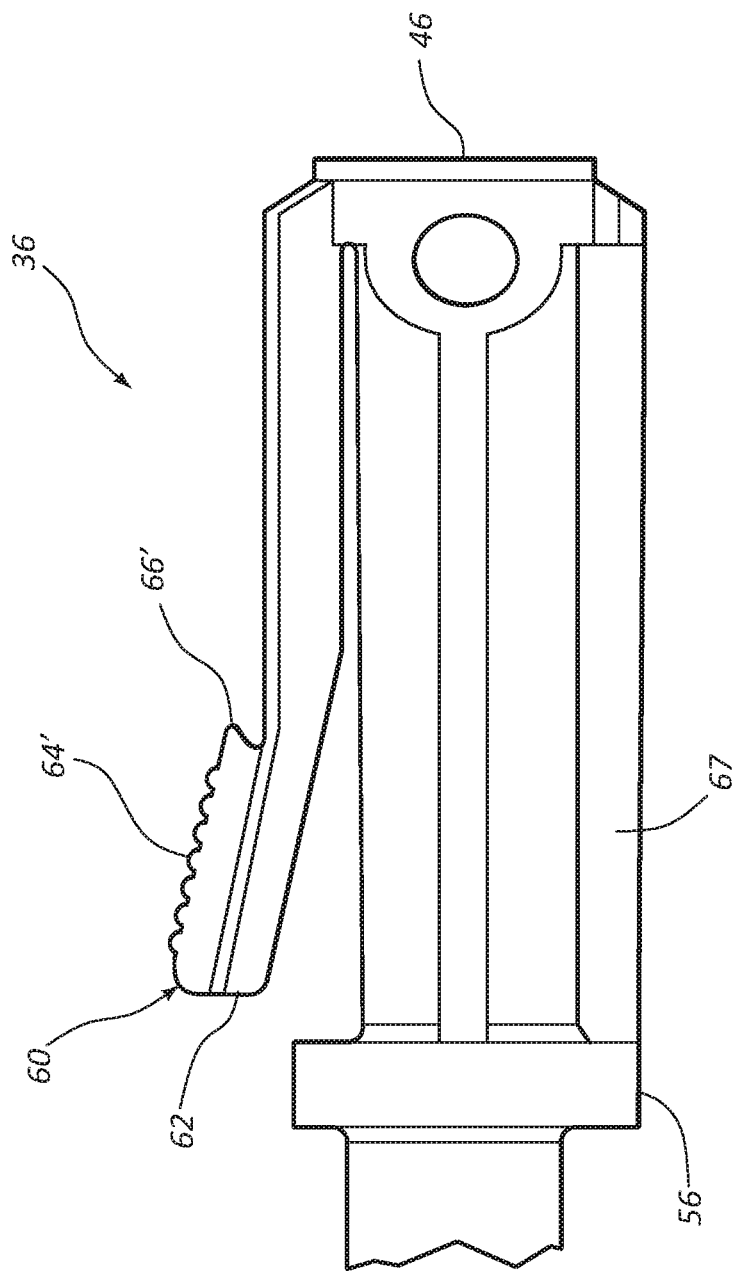
FIG. 18A is a blown up side elevation view of an alternative embodiment of a needle hub.
Figure 18B:
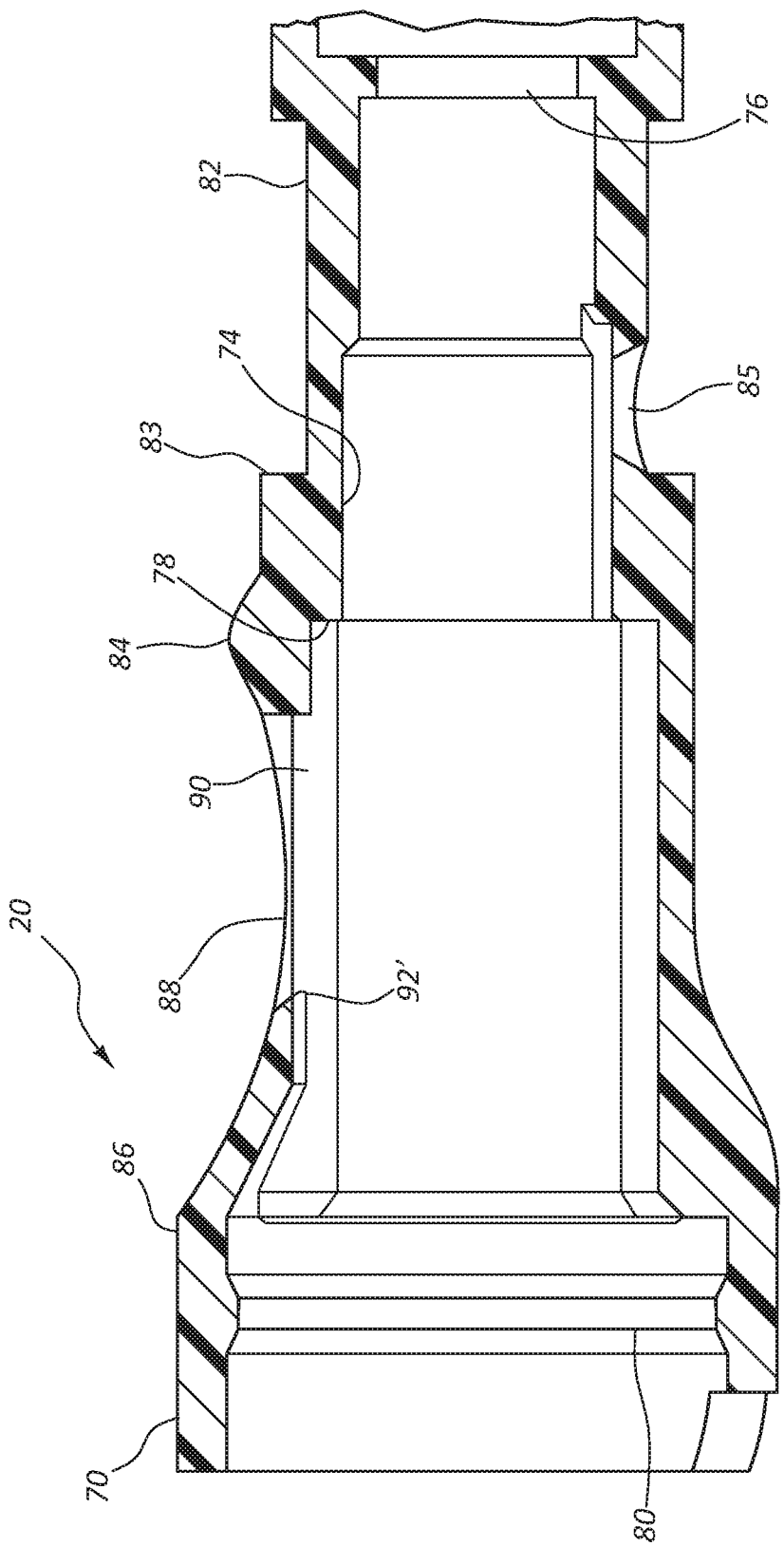
FIG. 18B is a blown up cross-sectional view of a portion of an alternative embodiment of the barrel assembly.
Figure 18C:
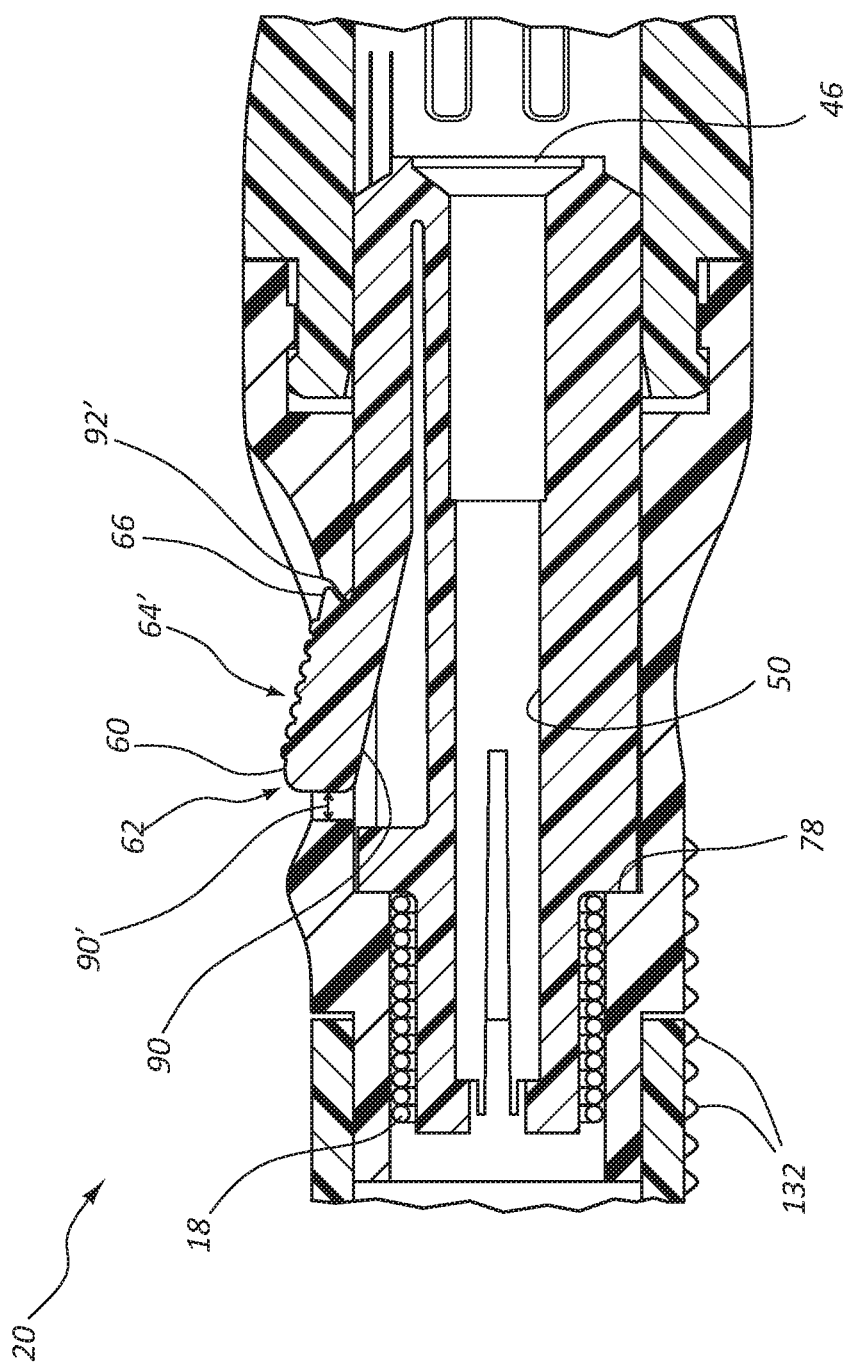
FIG. 18C is a blown up cross-sectional view of the needle hub of FIG. 18A located within the barrel assembly of FIG. 18B.

As mentioned above, additional embodiments are contemplated for reducing or preventing incidents of inadvertent actuation or depression of actuator button 64 and/or the premature deactivation of device 10. With reference to FIGS. 18A through 18C, for example, some embodiments require a two-step deactivation process. As illustrated in FIG. 18A, in some embodiments, actuator arm 60 includes an interlocking edge 66'. In such embodiments button 64' includes texture, raised bumps or protrusions, ridges, grooves, or other means for enhancing the frictional surface of button 64'. As seen in FIG. 18B, in such embodiments, distal barrel 20 includes a correspondingly shaped interlocking edge 92'. With reference to FIG. 18C, interlocking edges 66' and 92' are configured for interlocking or mating engagement with one another when device 10 is active, i.e., when needle 34 is exposed for insertion into the vasculature of a patient.

According to some embodiments, in order to deactivate device 10, i.e., to release the energy stored in spring 18 in order to fully retract needle assembly 16 proximally, a user must first push needle assembly 16 distally a sufficient distance to disengage interlocking edges 66' and 92'. The raised or textured surface of button 64' facilitates the user's frictional grip of button 64'. Such a configuration permits the user to adequately apply axial force in the distal direction via button 64' to needle assembly 16. In this way, the user temporarily overcomes the proximal force of spring 18 and moves needle assembly 16 distally far enough to disengage interlocking edges 66' and 92'. Following disengagement of interlocking edges 66' and 92' the user then depresses cantilevered actuator arm 60 and deactivates device 10 as described previously.

In various embodiments, the raised or textured surface of button 64' has a sufficiently low profile so as not to interfere with the retraction process once actuator arm 60 is depressed and needle assembly 16 retracts. In some further embodiments, a gap 90' between the distal edge of aperture 90 and the distal end 62 of actuator arm 60 is slightly larger than the interlocking depth of interlocking edges 66' and 92'. This configuration permits needle assembly 16 to move far enough distally to permit the disengagement of interlocking edges 66' and 92'.

Additional embodiments are also contemplated. For example, in some embodiments, actuator button 64' and actuator arm 60 are separate components coupled together via a spring mounting configuration. In this way, button 64' is biased in a locked position and can be moved distally sufficiently to allow interlocking edges 66' and 92' to disengage independently from moving the entire needle assembly distally. Once interlocking edges 66' and 92' are disengaged, actuator arm 60 is depressed and device 10 is deactivated as previously described. In such embodiments, the spring force between button 64' and actuator arm 60 is less than the spring force provided by spring 18.

In the embodiments described with reference to FIGS. 18A through 18C, the mating engagement of interlocking edges 66' and 92' under the proximal biasing force of spring 18 prevent or minimize incidents of premature deactivation of device 10 via the two-step process discussed above. Nevertheless, deactivation of device 10 may still be accomplished with a simple one-handed operation thus leaving the user's other hand free for other tasks.

Figure 19A:
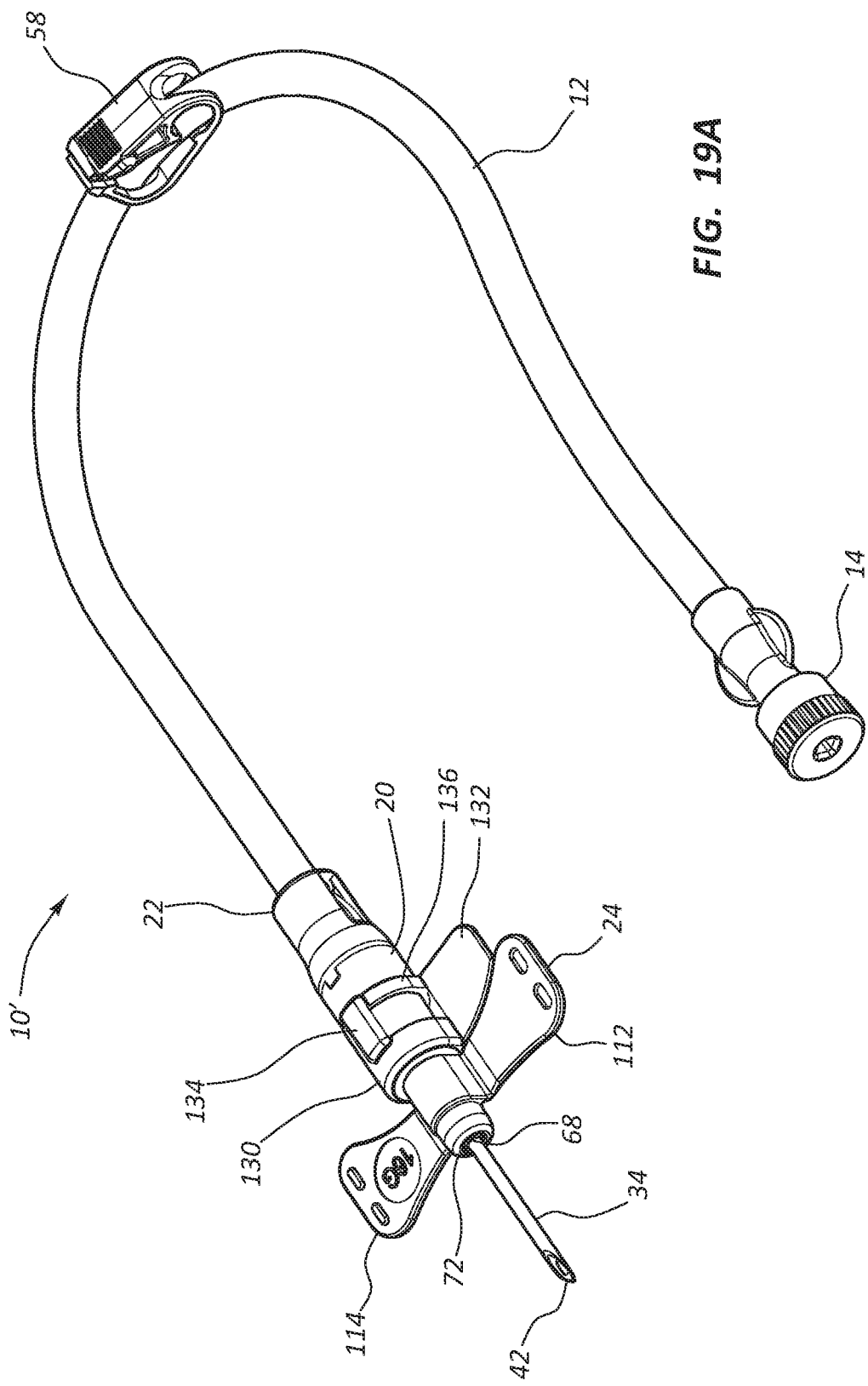
FIG. 19A is a perspective view of an alternative embodiment of a fluid collection or infusion device or set having a safety sleeve in accordance with various embodiments.

With reference to FIGS. 19A through 19C, yet additional embodiments for reducing or preventing incidents of inadvertent depression of actuator button 64 and the premature retraction of needle assembly 16 are contemplated. As illustrated, in addition to one or more of the various components or features previously described, device 10' further includes an annular sleeve or protective ring 130. In some embodiments, sleeve 130 forms an outer band or barrel which slips over distal barrel 20 prior to affixing wing attachment 24 thereto. In other embodiments, sleeve 130 is an incomplete band or barrel that extends through approximately 270° around the circumference of distal barrel 20 and which can snap over distal barrel 20 during the assembly process, including after wing attachment 24 has already been installed. In various embodiments, the inside diameter of sleeve 130 is sized relative to the outside diameter of distal barrel 20 such that sleeve 130 snugly but rotatably fits around the circumference of distal barrel 20. According to various alternative embodiments, sleeve 130 is comprised of plastic materials, such as polycarbonate, polypropylene, polyethylene, acrylic, polystyrene, ABS and/or other plastic materials, or combinations of plastic materials, having desirable properties, including sufficient flexibility and rigidity to operate as described herein.

According to some embodiments, sleeve 130 includes or defines an activation tab 132, a safety cover 134, and an access slot, cavity or opening 136. Sleeve 130 is rotatably coupled to distal barrel 20 such that cover 134 covers, obscures, or is otherwise over button 64. Cavity 136 is located adjacent one side or the other of button 64 while device 10' is active. In some embodiments, activation tab 132 occupies a plane in common with wing attachment 24 while device 10' is active. In this configuration, cover 134 prevents a user from inadvertently depressing button 64. Nevertheless, sleeve 130 does not obstruct or otherwise interfere with the use of device 10' as described in detail previously. As shown in FIG. 19B, in various embodiments, prior to deactivating device 10', cavity 136 extends around the circumference of sleeve 130 from approximately adjacent one side or the other of button 64 through approximately 180°. In other embodiments, cavity or slot 136 comprises a window sufficiently wide to allow a user to access button 64 therethrough and thus extends circumferentially through a width approximately consistent with the width of an average user's fingertip.

According to some embodiments, as illustrated in FIG. 19C, in order to deactivate device 10', i.e., to release the energy stored in spring 18 in order to fully retract needle assembly 16, a user must first rotate sleeve 130 via tab 132 in a direction 138 until button 64 is exposed through opening 136. In some embodiments, a user continues to rotate sleeve 130 until button 64 is sufficiently exposed to allow the user to depress button 64 with his or her fingertip. In other embodiments, a user rotates sleeve 130 through approximately 180°, or until tab 132 reoccupies the plane defined by wing attachment 24 on the opposite side of distal barrel 20 from where tab 132 was initially oriented. For example, in some embodiments, tab 132 is initially adjacent side 112 of wing attachment 24 and, following rotation of sleeve 130, tab 132 is adjacent side 114 of wing attachment 24. Following a sufficient rotation of sleeve 130 as described above, the user can then depress cantilevered actuator arm 60 via button 64 and deactivate device 10' as described previously.

According to some embodiments, sleeve 130 is retained against rotation in a direction opposite to the direction in which it is intended that sleeve 130 be rotated to expose button 64. In this way, button 64 is prevented from inadvertent activation via coming in contact with the inside diameter of sleeve 130 due to a reverse rotation thereof. For example, in some embodiments, cover 134 is sized and configured to cover button 64 as well as the apexes of distal major diameter portion 84 and proximal major diameter portion 86 of distal barrel 20. Sleeve 130 is prevented from inadvertent rotation in the wrong direction as the inside diameter of sleeve 130 is obstructed by the apexes of distal major diameter portion 84 and proximal major diameter portion 86 of distal barrel 20. Cover 134 and slot 136, on the other hand, are configured to accommodate the apexes of distal major diameter portion 84 and proximal major diameter portion 86 of distal barrel 20 when sleeve 130 is rotated in the intended direction. Thus, button 64 is prevented from inadvertent activation and is protected by the interaction of cover 134 and the distal and proximal major diameter portions 84 and 86 of distal barrel 20.

According to various embodiments, the methods and structures disclosed herein enable a user to safely handle devices 10 and/or 10' during removal from associated packaging, insertion into a patient's vasculature, use of such devices, and securement of such devices until an associated medical procedure is complete without inadvertently and prematurely deactivating devices 10 and/or 10'. In some embodiments, while two steps are required to deactivate the device, deactivation can be performed in a single-handed operation. Upon deactivation, devices 10 and/or 10' provide protection from both needle stick injuries as well as containing residual blood and preventing blood drips or leaks via septum 68

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A sealed retractable needle assembly, comprising: a needle assembly comprised of a needle hub and a needle securely coupled to the needle hub; a resiliently deflectable actuator arm extending from the needle hub and having an actuator button formed thereon; a barrel having proximal and distal ends and a passage extending therebetween, wherein the needle assembly is slidably disposed within the passage and the needle assembly and the resiliently deflectable actuator arm are axially movable relative to the barrel from a distal position where the needle projects distally beyond the distal end of the barrel and a proximal position where the needle is entirely contained within the barrel, and wherein the barrel defines an aperture extending therethrough, which aperture engages the actuator button when the needle hub is in the distal position and the actuator button disengages the aperture when the resiliently deflectable actuator arm is resiliently deflected; a spring disposed in the barrel for propelling the needle assembly to the proximal position when the resiliently deflectable actuator arm is deflected and the actuator button disengages the aperture; and a septum fitted within the distal end of the barrel, wherein the needle extends through the septum when the needle is in the distal position, and wherein the septum seals the barrel when the needle is in the proximal position; an annular sleeve rotatably disposed about a circumference of the proximal end of the barrel, wherein the annular sleeve is selectively rotatable between a first position and a second position, and wherein the annular sleeve comprises a cover and a slot, wherein the annular sleeve prevents the needle assembly from being inadvertently propelled into the proximal position when the annular sleeve is in the first position, and wherein the annular sleeve must be rotated to the second position before the resiliently deflectable actuator arm can be deflected such that the actuator button disengages the aperture and the needle assembly is propelled under the spring force into the proximal position.

2. The sealed retractable needle assembly of claim 1, further comprising an absorbent sponge fitted in proximity to the septum within the distal end of the barrel, wherein the needle extends through the sponge when the needle is in the distal position, and wherein the sponge absorbs and retains any fluid on the outside of the needle as the needle is retracted into the proximal position.

3. The sealed retractable needle assembly of claim 1, wherein the slot extends 180° around a circumference of the annular sleeve.

4. The sealed retractable needle assembly of claim 3, wherein the cover obscures the aperture and the actuator button when the sleeve is in the first position, and wherein the aperture and the actuator button are accessible through the slot when the sleeve is in the second position.

5. A sealed retractable needle assembly, comprising:
a needle assembly comprised of a needle hub and a needle securely coupled to the needle hub;
a resiliently deflectable actuator arm extending from the needle hub and having an actuator button formed thereon;
a barrel having proximal and distal ends and a passage extending therebetween, wherein the needle assembly is slidably disposed within the passage such that the needle assembly and the resiliently deflectable actuator arm are axially movable relative to the barrel from a distal position where the needle projects distally beyond the distal end of the barrel and a proximal position where the needle is entirely contained within the barrel, and wherein the barrel defines an aperture extending therethrough, which aperture engages the actuator button when the needle hub is in the distal position and the actuator button disengages the aperture when the resiliently deflectable actuator arm is resiliently deflected;

a spring disposed in the barrel for propelling the needle assembly to the proximal position when the resiliently deflectable actuator arm is deflected and the actuator button disengages the aperture;

a septum fitted within the distal end of the barrel, wherein the needle extends through the septum when the needle is in the distal position, and wherein the septum seals the barrel when the needle is in the proximal position; and an annular sleeve rotatably disposed about a circumference of the proximal end of the barrel, wherein the annular sleeve is selectively rotatable between a first position and a second position, and wherein the annular sleeve comprises a cover and a slot, wherein the cover obscures the aperture and the actuator button when the annular sleeve is in the first position, and wherein the aperture and the actuator button are accessible through the slot when the annular sleeve is in the second position.

6. The sealed retractable needle assembly of claim 5, further comprising an absorbent sponge fitted within the distal end of the barrel, wherein the needle extends through the sponge when the needle is in the distal position, and wherein the sponge absorbs and retains any fluid on the outside of the needle as the needle is retracted into the proximal position.

7. The sealed retractable needle assembly of claim 6, further comprising at least one resiliently deflectable locking finger extending from the barrel, wherein the at least one locking finger is configured to lockingly engage the needle hub when the needle hub reaches the proximal position.

8. The sealed retractable needle assembly of claim 7, wherein the annular sleeve prevents the needle assembly from being inadvertently propelled into the proximal position when the annular sleeve is in the first position, and wherein the annular sleeve must be rotated to the second position before the resiliently deflectable actuator arm can be deflected such that the actuator button disengages the aperture and the needle assembly is propelled under the spring force into the proximal position.

9. A scaled retractable needle assembly, comprising: a needle assembly comprised of a needle hub and a needle securely coupled to the needle hub; a resiliently deflectable actuator arm extending from the needle hub and having an actuator button formed thereon; a barrel having proximal and distal ends and a passage extending therebetween, wherein the needle assembly is slidably disposed within the passage such that the needle assembly and the resiliently deflectable actuator arm are axially movable relative to the barrel from a distal position where the needle projects distally beyond the distal end of the barrel and a proximal position where the needle is entirely contained within the barrel, and wherein the barrel defines an aperture extending therethrough, which aperture engages the actuator button when the needle hub is in the distal position and the actuator button disengages the aperture when the resiliently deflectable actuator arm is resiliently deflected; a spring disposed in the barrel for propelling the needle assembly to the proximal position when the resiliently deflectable actuator arm is deflected and the actuator button disengages the aperture; a septum fitted within the distal end of the barrel, wherein the needle extends through the septum when the needle is in the distal position, and wherein the septum seals the barrel when the needle is in the proximal position; and an annular sleeve rotatably disposed about a circumference of the proximal end of the barrel, wherein the annular sleeve is selectively rotatable between a first position and a second position, and wherein the annular sleeve comprises a cover and a slot, wherein the sleeve prevents the needle assembly from being inadvertently propelled into the proximal position when the sleeve is in the first position, and wherein the sleeve must be rotated to the second position before the resiliently deflectable actuator arm can be deflected such that the actuator button disengages the aperture and the needle assembly is propelled under the spring force into the proximal position.

10. The sealed retractable needle assembly of claim 9, further comprising at least one resiliently deflectable locking finger extending from the barrel, wherein the at least one locking finger is configured to lockingly engage the needle hub when the needle hub reaches the proximal position.

11. The sealed retractable needle assembly of claim 9, wherein the barrel comprises a channel aligned with the aperture and configured to slidably receive the resiliently deflectable actuator arm.

12. The sealed retractable needle assembly of claim 9, wherein the needle assembly and the resiliently deflectable actuator arm are axially movable relative to the barrel.

13. The sealed retractable needle assembly of claim 9, wherein the passage comprises a distal flange defining a distal stop for a distal end of the spring such that the spring is compressed within the barrel.

14. The sealed retractable needle assembly of claim 9, further comprising an absorbent sponge fitted within the distal end of the barrel.

15. The sealed retractable needle assembly of claim 14, wherein the needle extends through the sponge when the needle is in the distal position, and wherein the sponge absorbs and retains any fluid on the needle as the needle is retracted into the proximal position.

* * * * *